United States Patent
Hadden et al.

Patent Number: 5,614,504
Date of Patent: Mar. 25, 1997

[54] METHOD OF MAKING INOSINE MONOPHOSPHATE DERIVATIVES AND IMMUNOPOTENTIATING USES THEREOF

[75] Inventors: John W. Hadden; Alfredo Giner-Sorolla, both of Tampa, Fla.

[73] Assignee: The University of South Florida, Tampa, Fla.

[21] Appl. No.: 426,682

[22] Filed: Apr. 21, 1995

Related U.S. Application Data

[63] Continuation-in-part of Ser. No. 995,550, Dec. 22, 1992, abandoned, which is a continuation of Ser. No. 561,979, Aug. 1, 1990, abandoned.

[51] Int. Cl.$^6$ ............................ C07H 19/20; A61K 31/70
[52] U.S. Cl. ........................ 514/45; 536/27.8; 536/26.7
[58] Field of Search ............................ 514/45; 536/27.8, 536/26.7

[56] References Cited

U.S. PATENT DOCUMENTS

| | | | |
|---|---|---|---|
| 3,560,478 | 2/1971 | Myers | 536/26.2 |
| 3,575,958 | 4/1971 | Nagasawa et al. | 536/26.7 |
| 3,728,450 | 4/1973 | Gordon | 514/45 |
| 3,791,932 | 2/1974 | Schuurs et al. | 435/7.8 |
| 3,839,153 | 10/1974 | Schuurs et al. | 435/7.93 |
| 3,850,578 | 11/1974 | McConnell | 436/536 |
| 3,850,752 | 11/1974 | Schuurs et al. | 435/7.93 |
| 3,853,987 | 12/1974 | Dreyer | 424/1.37 |
| 3,857,940 | 12/1974 | Gordon | 514/45 |
| 3,867,517 | 2/1975 | Ling | 436/531 |
| 3,879,262 | 4/1975 | Schuurs et al. | 435/7.93 |
| 3,901,654 | 8/1975 | Gross | 436/172 |
| 3,935,074 | 1/1976 | Rubenstein et al. | 435/7.9 |
| 3,984,533 | 10/1976 | Uzgiris | 436/516 |
| 3,996,345 | 12/1976 | Ullman et al. | 436/537 |
| 4,034,074 | 7/1977 | Miles | 436/518 |
| 4,098,876 | 7/1978 | Piasio et al. | 436/500 |
| 4,221,794 | 9/1980 | Simon et al. | 514/261 |
| 4,221,909 | 9/1980 | Simon et al. | 544/265 |
| 4,221,910 | 9/1980 | Giner-Sorolla | 544/265 |
| 4,340,726 | 7/1982 | Simon et al. | 536/17.4 |
| 4,387,226 | 6/1983 | Hadden et al. | 544/247 |
| 4,389,395 | 6/1983 | Lerner et al. | 424/85 |
| 4,439,196 | 3/1984 | Higuchi | 424/473 |
| 4,447,224 | 5/1984 | DeCant, Jr. et al. | 604/67 |
| 4,447,233 | 5/1984 | Mayfield | 604/152 |
| 4,457,919 | 7/1984 | Simon et al. | 514/32 |
| 4,486,194 | 12/1984 | Ferrara | 424/449 |
| 4,487,603 | 12/1984 | Harris | 604/152 |
| 4,510,144 | 4/1985 | Hadden et al. | 514/257 |
| 4,512,981 | 4/1985 | Gordon | 514/45 |
| 4,879,219 | 11/1989 | Wands et al. | 435/5 |
| 4,950,652 | 8/1990 | Carter | 514/44 |
| 5,011,771 | 4/1991 | Bellet et al. | 435/7.94 |

FOREIGN PATENT DOCUMENTS

| | | |
|---|---|---|
| 58-140100 | 8/1993 | Japan . |

OTHER PUBLICATIONS

Specter et al., "New Approaches to Immunotherapy: Thymometric Drugs," *Springer Sem. Immunopath.*, 8(4), 375–385 (1985); *Chem. Abstr.*, 104(11), 81361j (1986); only CA Abstract provided.

Nichol et al., "Studies on Phosphate Binding Sites of Inosinic Acid Dehydrogenase and Adenylosuccinate Synthetase," *Biochemistry*, 6(4), 1008–1015 (1967).

Rosen et al., *Dictionary of Immunology*, M Stockton Press, New York, NY, 1989, p. 110.

W. S. Zielinski, "An Improved Synthetic Route to the β-Hydroxy Esters of 5'-Nucleotides," *Nucleic Acids Res.*, 3(7), 1769–1775 (1976).

Miller et al., "Models for the Interaction of $Zn^{2+}$ with DNA. The Synthesis and X–ray Structural Characterization of Two Octahedral Zn Complexes with Monomethyl Phosphate Esters of 6–Oxopurine 5'–Monophosphate Nucleotides," *J. Am. Chem. Soc.*, 107(4), 1048–1055 (1985).

H. G. Khorana, "Studies on Polynucleotides. VII. Approaches to the Marking of Ends Groups in Polynucleotide Chains: The Methylation of Phosphomonoester Groups," *J. Am. Chem. Soc.*, 81, 4657–4660 (1959).

(List continued on next page.)

*Primary Examiner*—John Kight
*Assistant Examiner*—L. Eric Crane
*Attorney, Agent, or Firm*—Kohn & Associates

[57] ABSTRACT

A method of making inosine-5'-monophosphate and its derivatives resistant to 5'-nucleotidase by chemically modifying inosine-5'-monophosphate to the formula:

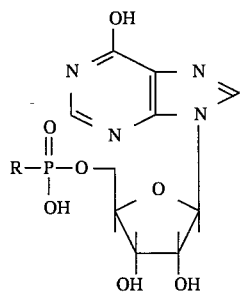

wherein R is selected from the group consisting of an alkyl, alkoxy and secondary amino compounds whereby inosine-5'-monophosphate biological activity is retained in vitro and extended to in vivo.

27 Claims, 9 Drawing Sheets

OTHER PUBLICATIONS

Hadden, "Immunostimulants," *Trends in Pharmacology*, 14, 169–174 (1993).

Hadden, "Immunotherapy of Human Immunodeficiency Virus Infection," *Trends in Pharmacology*, 12, 107–111 (1991).

Hadden et al., "Methyl Inosine Monophosphate (MIMP), A New Purine Immunomodulator for HIV Infection," *Intl. J. Immunopharmacol.*, 13(Suppl. 1), 49–54 (1991).

Hadden et al.(II), "Methyl Inosine Monophosphate: A Potential Immunotherapeutic for Early Human Immunodeficiency Virus (HIV) Infection," *Intl. J. Immunopharmacol.*, 14(4), 555–563 (1992).

Moffatt et al., "Nucleoside Polyphosphates. X. The Synthesis and Some Reactions of Nucleoside-5'-Phosphoromorpholidates and Related Compounds. Improved Methods for the Synthesis of Nucleoside-5'-Polyphosphates," *J. Am. Chem. Soc.*, 83, 649–659 (1961).

R. S. Root–Bernstein(I), "AIDS Is More Than HIV: Part I," *Genetic Engineering News*, Sep. 1, 1992, pp. 4–6.

R. S. Root–Bernstein(II), "AIDS Is More Than HIV: Part II," *Genetic Engineering News*, Sep. 15, 1992, pp. 4–5.

Hadden et al.(III), "Methyl Inosine Monophosphate (MIMP), A New Purine Immunomodulator fo HIV Infection," *International Journal of Immunopharmacology*, 13(Suppl. 1), 49–54 (1991).

Alper et al., "Genetic prediction of nonresponse to hepatitis B vaccine" *New Engl. J. Med.*, 321:708–712 (1989).

Benacerraf and McDevitt, "Histocompatibility–linked immune response genes" *Science*, 174:273–279 (1972).

Bogdan et al., "Macrophage deactivation by interleukin 10" *J. Exp. Med.*, 174:1549–1555 (1991).

Byars and Allison, "Immunologic adjuvants: general properties, advantages and limitations" in *Laboratory Methods in Immunology*, 2:40–52 (1989).

Carelli et al., "Persistent enhancement of cell–mediated and antibody immune responses . . . " *Infection and Immunity*, pp. 312–314, (1981).

Carswell et al., "An endotoxin–induced serum factor that causes necrosis of tumors" *Proc. Natl. Acad. Sci. USA* 72:3666–3670 (1975).

Chakkalath et al., "Leishmania major–parasitized macrophages augment Th2–type T cell activation" *J. Immunology*, 153: 4378–4387 (1994).

Drews, "Novel immunological pathways to the treatment of infections" *Infection*, 22, No. 3, (1994 *Fed. Proc.*, 29:684 (1970).

Fiorentino et al., "Two types of mouse T helper cell. IV. Th2 clones secrete a factor that inhibits cytokine . . . " *J. Exp. Med.*, 170:2081–2095 (Dec. 1989).

Glasky et al., "Isoprinosine, a purine derivative . . . " In *Proceedings of a Symposium and Workshop on Combined Immunodeficiency Disease . . .*, Academic Press, Inc. New York, NY (1975).

Grossman and Cohen, "Immunization" in *Basic and Clinical Immunology*. (Seventh Edition) Appleton & Lange, Norwalk, CT pp. 725–726 (1991).

Haak–Frendscho et al., "Administration of anti–IL–4 monoclonal antibody 11B11 increases the resistance of mice . . . " *J. Immunology*, 148:3978–3985, (1992).

Hadden, "The action of immunopotentiators in vitro on lymphocyte and macrophage activation" in *The Pharmacology of Immunoregulation*, pp. 370–383 (1978).

Hadden, "Thymomimetic drugs" in *Immunopharmacology*, Raven Press, NY, p. 183 (1985).

Hadden, "Immunotherapy in the treatment of infectious diseases" in Proceedings of the *Int'l Symposium on Immunological Adjuvants*, Alan R. Liss, NY, pp. 337–349 (1987).

Hadden et al., "Effects of levamisole and imidazole on lymphocyte proliferation and cyclic nucleotide levels" *Cell. Immun.*, pp. 98–103 (1975).

Hadden et al., "Levamisole and inosiplex: antiviral agents with immunopotentiating action" *NY Acad. Sci.*, 284:139–152 (1976).

Hadden et al., "Purine analogs as immunodolulators" in *Progress in Immunology IV.* (Academic Press, NY) pp. 1393–1408 (1983).

Hadden et al., "Effects of T–cell growth factor (interleukin–II) and thymic hormones on prothymocytes and immature thymocytes" (1986); Lymphokine Res., 5, Supp. 1, S49–S54.

Hadden et al., "Methyl inosine monophosphate (MIMP)—A new purine immunomodulator" *Int. J. Immunopharmacol.*, (abstract) 13:762 (1991a).

Hess et al., "Active immunization of homosexual men using a recombinant hepatitis B vaccine" *J. Med. Virol.*, 29:229 (1989).

Khorana, "Studies on polynucleotides. VII. Approaches to the marking of end groups in polynucleotide chains . . . " *J. Am. Chem. Soc.*, 81:4657–60 (1959).

MacDonald et al., "Requirement for a bacterial flora beore mice generate cells capable of mediating the delayed . . . " *J. Immunol.*, 122:2624–2629 (1979).

Meuer et al., "Low does interleukin–2 induces immune response against HBsAg in immunodeficient nonresponders . . . " *Lancet.*, 1–15 (1989).

Miller et al., "Models for the interaction of ZN with DNA. The synethesis and x–ray structural characterization . . . " *J. Am. Chem. Soc.*, 107:1048–55 (1985).

Mosmann and Coffman, "Th1 and Th2 cells: differential patterns of lymphokine secretion lead to different functional properties" *Ann. Rev. Immunol.* 7:151–173 (1989).

Sad and Mosmann, "Single IL–2–secreting precursor CD4 T cell can develop into either Th1 or Th2 cytokine . . . " *J. Immunology*, 3514–3522 (1994).

Saha et al., "Immunopotentiating activity of a nucleotide derivative, heptaminol AMP amidate (HAA) in mice . . . " *Research Communications in Chemical Pathology and Pharmacology*, 57(1):117–127 (Jul. 1987).

Saha et al., "Effect of heptaminol AMP amidate, a new nucleotide derivative, on In Vitro humoral immunity" *Japan J. Pharmacol.*, 47:63–69 (1988).

Sandrin et al., "Synthese d'esters adenosine–5–phosphoriques d'amino–alcools, comme inhibiteurs . . . " *Helvetica Chimica Acta.*, 49:76–82 (1966).

Scott, "IFN–y modulates the early development of Th1 and Th2 responses in a murine model of cutaneous leishmaniasis" *J. Immunol.*, 147: 3149 (1991).

Sosa et al., "Potentiation of immune response in mice by a new inosine derivative—methyl inosine monophosphate (MIMP)" *Int. J. Immunopharmacol.*, 14:1259–1266 (1992).

Stites and Terr, *Basic and Clinical Immunology*, Seventh Edition, Appleton & Lange, Norwalk, CT, p. 797 (1991).

Trinchieri, "Interleukin–12 and its role in the generation of Th1 cells" *Immunol. Today.*, 14:335 (1993).

Tripp et al., "Neutralization of IL–12 decreases resistance to listeria in SCID and C.B–17 mice" *J. Immunology*, 152:1883–1887 (1994).

Turner et al., "Studies on polynucleotides. VI. Experiments on the chemical polymerization of mononucleotides . . . " *J. Am. Chem. Soc.*, 81:4651–56 (1959).

METHOD OF MAKING INOSINE MONOPHOSPHATE DERIVATIVES AND IMMUNOPOTENTIATING USES THEREOF

This application is a continuation-in-part of U.S. Ser. No. 07/995,550, filed Dec. 22, 1992, which is a continuation of U.S. Ser. No. 07/561,979, filed Aug. 1, 1990, both now abandoned.

TECHNICAL FIELD

The present invention generally relates to methods for enhancing immune response by increasing the effectiveness of an immunopotentiating agent, inosine-5'-monophosphate, by making it resistant to 5'-nucleotidase actions and method of use of the protected agent. The present invention relates to methods of treatment for patients with tumors, viral and intracellular bacterial pathogens and to a vaccine adjuvant.

BACKGROUND OF THE INVENTION

Secondary immunodeficiencies are common in cancer, aging, autoimmunity, AIDS, and other viral and bacterial diseases. It has long been thought that treatment of these secondary immunodeficiencies would result in improved prognosis in these diseases. Despite much experimental effort, so far only levamisole and isoprinosine have been extensively licensed and employed clinically for such treatments. There is a need for more effective drugs of this type.

Immune function includes the humoral and cellular arms of the immune system as well as those aspects dependent on macrophages and granulocytes. The various aspects of immune function can be augmented or modified by various agents which can, in general, be referred to as immunopotentiators. Immunopotentiators, including drugs and biological substances, have been extensively employed in the prevention and treatment of human diseases.

However, recent work (Sad and Mosmann, 1994; Sieling et al., 1994; Chakkalath and Titus, 1994; Tripp et al., 1994; Bogdan et al., 1991; Fiorentino et al., 1989) suggests that improper stimulation of the immune response may actually facilitate the disease process. It appears in both murine and human models that the cytokine profile of immune response is regulated by which one of the subclasses of T helper (Th) cells, Th1 or Th2, is activated in response to the pathogens. Tht cells, in general, have a pattern of secreting IL-2, IFN-γ and lymphotoxin, while the Th2 general secretion pattern is IL-4, IL-5, IL-6, IL-9, IL-10 and IL-13. The Th1 cell cytokine profiles are generally associated with disease resistance and Th2 cytokine profiles with progressive disease. In particular, it has been shown that for intracellular pathogens, such as *Mycobacterium leprae, Listeria monocytogenes* and *Leishmania major*, the cytokine profile from Th1 cells is necessary to restrict the growth of the pathogens. Many factors determine which subset of T-cells is activated during the immune response and it appears that it is a combination of factors, including IL-12 from activated macrophages, that lead to a Th1 response. In these diseases, it would be useful to have a means of augmenting or stimulating the Th1 response. For example in leprosy, patients do not express the type 1 response, rather their lesions express the type 2 cytokines which are typical of humoral responses and immunosuppression of the cell mediated immunity needed for resistance to intracellular pathogens.

One class of immunopotentiators has been derived from purine structures such as inosine or hypoxanthine, e.g., isoprinosine (a synthetic drug complex composed of inosine and the p-acetamido-benzoate salt of N,N-dimethylamino-2-propanol in a molar ratio of 1:3; DIP salt).

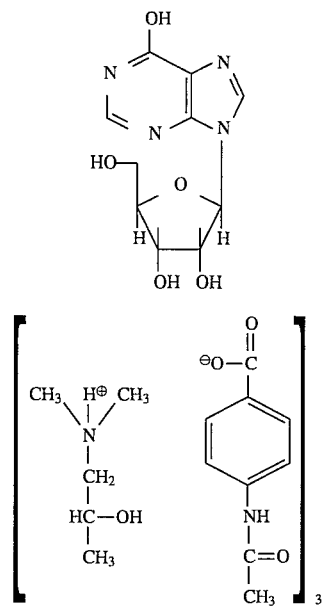

and NPT 15392 (9-erythro-2-hydroxy-3-nonyl-hypoxanthine)

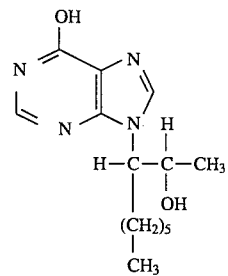

These compounds have been classified as "thymomimetic drugs" (Hadden, 1985) in that they stimulate the immune system by actions primarily on thymus-derived (T) lymphocytes, although they do act on other cells involved in immune responses. Isoprinosine is one example of a medically useful thymomimetic drug which is licensed for human use in a number of countries around the world. The action of isoprinosine in vitro is paralleled by inosine and potentiated by the complex with DIP salt (Hadden, 1978). The action of isoprinosine in vivo is not achieved with inosine or DIP salt alone (Wybran et al., 1982), suggesting to applicants that complex formation and protection of the inosine base is critical for in vivo activity.

The search for more immunologically active molecules of this type for clinical use has generated a considerable literature. U.S. Pat. No. 3,728,450 to Gordon discloses complexes formed by inosine and amino-alcohols which have pharmacological activity in combatting influenza or herpes virus.

U.S. Pat. No. 4,221,794 to Hadden et al. discloses complexes of purine derivatives (9-(hydroxyalkyl) purines) with amino-alcohol salts of p-acetamidobenzoic acid which have immunomodulating and antiviral activity.

U.S. Pat. No. 4,221,909 to Hadden et al. discloses p-acetamidobenzoic acid salts of 9-(Hydroxyalkyl) purines useful as viricides, immunoregulators and anti-leukemia agents.

U.S. Pat. No. 4,340,726 to Giner-Sorolla et al. discloses esters (purine compounds) having immunomodulator, antiviral, antitumor and enzyme inhibitor activity.

U.S. Pat. No. 4,221,910 to Giner-Sorolla et al. discloses 9-(hydroxyalkyl) purines useful as immunopotentiators, viricides and antileukemic agents.

U.S. Pat. No. 4,457,919 to Giner-Sorolla et al. discloses purine derivatives which have immunomodulating, antiviral and antitumor activity.

U.S. Pat. Nos. 4,510,144 and 4,387,226, to Giner-Sorolla et al., disclose dihydrothiazolo purine derivatives with immunomodulating activity.

Japanese Laid-Open Patent Application Number 58-140100 discloses (heptamin-1-ol)-5'-adenosine-monophosphate. Saha et al. (1988) discloses its activity in potentiating the in vitro primary humoral immune response against a T cell-dependent antigen (sheep red blood cells) when present in the early phase of spleen cell culture. Saha et al. (1987) discloses the activity of HAA in augmenting anti-SRBC PFC activity and antibody titer values in ICR male mice. They also show the activity of HAA in increasing anti-SRBC PFC activity and antibody titer values in spontaneously hypertensive rats.

Hadden et al. [1983] indicates that purines, particularly inosine-containing or inosine-like compounds, where examined, generally share the capacity to mimic thymic hormone action to induce precursor T-cell differentiation and to potentiate functional responses of mature T-cells, particularly the Th1 cells in response to infections of intracellular pathogens. One example of these molecules, transfer factor, was hypothesized to contain inosine-5'-monophosphate (IMP) in its more elaborate structure (Wilson and Fudenberg, 1984).

It would be useful to have available these immunomodulating/immunopotentiating compounds for use as discussed herein below.

Viral infections and intracellular bacterial pathogens are a major public health concern. In both these categories, the bacterial and viral pathogens avoid the host immune system because they grow within the host's cells. A cell-mediated immune (CMI) response by Th1 cells initiated by macrophages is the general mode of host defense or resistance against intracellular pathogens once infection has occurred. An effective antibody response in response to vaccination can confer immunity.

While treatment for the bacterial diseases via antibiotics is available, the increasing drug resistance of bacteria makes it necessary to look at other avenues for treatment. One way of treating infected individuals is to increase the effectiveness of their immune system. In these diseases, the presence of sensitized T lymphocytes and activated macrophages is the key factor in immunity. Therefore, effective treatments for these diseases must activate macrophages and sensitize the appropriate T lymphocytes (Ryan in Stites and Terr, pages 637–645 and Mills in Stites and Terr, pages 646–656).

Intracellular bacterial pathogens include Salmonella, Legionella, Listeria, Mycobacteria and Brucella. Salmonella species are members of the Enterobacteriaceae and cause a significant portion of enteric disease, including typhoid fever. The capsule of S. typhi has a surface capsular antigen and antibody against the capsular antigen is not protective. In fact, many carriers of typhoid have high levels of antibodies against the pathogen.

Studies of Legionella show that it is an obligate intracellular parasite of macrophages. Lisreria is gram-positive causing meningeal infections and sepsis in adults and a variety of infections in neonates. The primary role of defense against these pathogens has been shown to be T-lymphocyte associated macrophage activation. Studies of Bruceila associated disease have also shown that antibody does not confer protection and that activated macrophages produced by specifically sensitized T-lymphocytes do protect.

It would be useful to have effective drugs for these diseases that activate macrophages and sensitize the appropriate T lymphocytes to the pathogen.

In general, there are few or no effective anti-viral drugs and, therefore, protection from viral pathogens also remains a major public health goal. Vaccination remains the best source of protection in viral diseases. However, often vaccines do not confer immunity because of: (1) a poorly immunogenic viral antigen; (2) the lack of time between vaccination and exposure; or (3) the inability of the vaccinated individual to respond.

For example, influenza vaccines must constantly be updated as the virus undergoes antigenic variation. Often the most current vaccine is not available, or not in full production, prior to the start of the winter months, which are the peak epidemic months. Therefore, those receiving the vaccine may be exposed to the virus in the environment before antibody titers are available. Further, among patients at higher risk, i.e. elderly and young, there is often a reduced compliance until an epidemic starts. In addition, influenza strikes particularly hard in the young and elderly populations and also individuals with underlying cardiorespiratory disease. These particular groups often have a less vigorous immune response to the vaccine.

Influenza viral infection suppresses normal pulmonary antibacterial defenses so that patients recovering from influenza have a greatly increased risk of developing bacterial pneumonia. It appears that there is an impairment of alveolar macrophages or neutrophils during influenza viral infection.

Therefore, a means of enhancing the immune response to influenza viral infection or of enhancing resistance to bacterial pneumonia would be useful in treating this disease. One possible way of increasing the efficacy of treatment is by treating with substances possessing immunopotentiating properties (Hadden et al., 1976; Hadden, 1987).

Chronic hepatitis B infection is a major public health concern. The hepatitis B virus is the cause of acute and chronic hepatitis, as well as hepatic carcinoma. The acute disease is self-limiting while the chronic infection persists for the life of the host. Chronic carriers remain infectious for life. It is estimated that there are over 100 million carriers world wide.

There are no currently effective treatments for the disease. Prevention, via vaccination, remains the only solution. Vaccination for those at risk is critical (James et al., 1991; Mills, 1991). However, upon vaccination with hepatitis B virus surface antigen (HBsAg), nearly 2% to 15% of those vaccinated have been found not to produce antibodies to the hepatitis B virus surface antigen (anti-HBs) and are thus not protected against this infection, in other words, they are nonresponders (Deinhardt, 1983). Various schemes of multiple administrations of the antigen preparation are recommended to induce intense immunity against hepatitis B (Grossman and Cohen, 1991). However, there is still a pool of nonresponders. Therefore, an alternative means of enhancing the immunogenicity of vaccine preparations against hepatitis B is needed to solve this important public health need.

People at high risk of infection are most frequently found among patients undergoing chronic hemodialysis treatment (Ferguson, 1990; Walz et al., 1989), those with HIV-infection and other immunocompromised patients (Hess et al., 1989). Those who come into contact with these groups and have not previously had contact with hepatitis B virus, face the highest risk of infection and, therefore, need rapid and maximal protection from the infection. This is particularly acute among health-care providers (Grossman and Cohen, 1991). Therefore, nonresponders to the currently available vaccine against hepatitis B in these groups are at even greater risk of infection.

It would be useful to be able to increase the efficacy of vaccination within the nonresponder groups. One possible way of increasing the efficacy of prophylaxis is the enhancement of the immunogenicity of available vaccines by using biologically active substances possessing adjuvant properties (Byars and Allison, 1989).

It is well known that adjuvants are able to stimulate antibody formation in response to heterologous antigens. Adjuvants are defined as compounds capable of potentiating an immune response and are, therefore, one class of immunopotentiators (Stites and Terr, 1991). Adjuvants are used to increase the immune response in vaccination (Seaman, 1991). For example, in vaccine preparations with hepatitis B, HBsAg is generally absorbed onto aluminum hydroxide to enhance the immunogenic effect in order to achieve a protective titer of anti-HBs (>10 IU/l) which prevents infections.

However, as stated above, there is a group of nonresponders who do not respond even to this augmented vaccine (Celis et al., 1987; Meuer et al., 1989). This lack of protective immunity by vaccination appears due, in part, to components of the immune response determined at the level of the major histocompatibility complex (MHC) (Alper et al., 1989; Walker et al., 1981). It has been suggested that "non-responders" lack a dominant gene of the immune response in the MHC and, as a result, synthesis of anti-HBs occurs, at most, at low levels that can barely be detected by currently applied methods of detection (Thomson et al., 1977). Similarly, immune response genes associated with the murine major histocompatibility complex (H-2) have been shown to control cellular and humoral responses to determinants on numerous T-cell-dependent antigens, including HBsAg.

The results obtained in combined application of hepatitis B vaccine and various immunomodulators point to the expediency of this approach, since combination treatment can reduce the number of persons who either do not completely respond or respond with low levels of anti-HBs (Celis et al., 1987; Meuer et al., 1989). However, while the data are encouraging, there still exist persons who do not respond to these treatments and for whom it would be useful to have an adjuvant boosted hepatitis B vaccine which promotes rapid induction of maximal levels of specific antibodies and increase protection in the nonresponder population.

Hadden et al. (1983) indicates that purines, particularly inosine-containing or inosine-like compounds, where examined, generally share the capacity to mimic thymic hormone action to induce precursor T-cell differentiation and to potentiate functional responses of mature T-cells.

Isoprinosine has shown some efficacy in the treatment of lethal influenza challenge in mice; and, when administered with a subinfectious dose of virus, it prevented mortality on subsequent challenge with virus (Glasky, 1985). Isoprinosine is licensed in several countries for human use in influenza therapy based upon its clinical activity in man (Glasky, 1985). However, the half-life of isoprinosine in man is less than four hours; and, therefore, it is not very effective for in vivo treatments. Isoprinosine is rapidly hydrolyzed, thereby causing the short half-life in vivo. Inosine in vitro (Hadden, 1978) has similar properties to isoprinosine, but in vivo it is rapidly catabolized so that its half-life is even shorter than isoprinosine and thus it has no activity in vivo (Wybran et al., 1982). It would be useful to have more stable inosine-like compounds with greater immunopotentiating capabilities.

SUMMARY OF THE INVENTION

According to the present invention, a method of making inosine-5'-monophosphate derivatives resistant to 5'-nucleotidase is provided by chemically modifying inosine-5'-monophosphate to the formula:

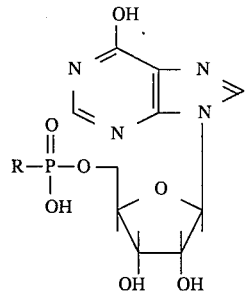

wherein R is selected from the group consisting of an alkyl, alkoxy and secondary amino compounds whereby inosine-5'-monophosphate biological activity is retained in vitro and extended to in vivo uses.

The present invention provides a method of potentiating the immune response of a mammal in need of treatment of immunogenic stimuli. The method comprises administering to the mammal an immunopotentiating effective amount of a 5'-nucleotidase resistant inosine-5'-monophosphate compound of the formula

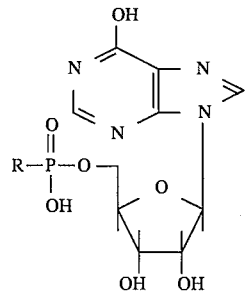

wherein R is a moiety which inhibits hydrolysis of the compound by 5'-nucleotidase and is selected from the group consisting of an alkyl, alkoxy and secondary amino compounds.

The present invention also provides a method for treating viral and intracellular bacterial pathogens in a mammal including the step of diagnosing a patient having an infectious disease caused by a pathogen selected from the group consisting of intracellular bacterial and viral pathogens. The method then provides for administering to the identified patients an effective amount of an immune stimulator 5'-nucleotidase resistant inosine-5'-monophosphate derivative having the formula

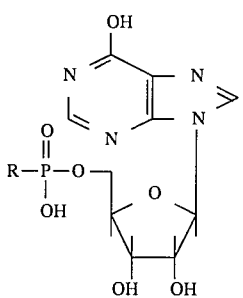

wherein R is selected from either an alkyl group from 1–6 carbon atoms, or an alkoxy group having the formula —$OR^1$, wherein $R^1$ is an alkyl group of from about 1–6 carbon atoms. In a preferred embodiment, an effective amount of Squalane can also be administered.

The present invention also provides a method of determining patients who will benefit from treatment with 5'-nucleotidase resistant inosine-5'-monophosphates. Peripheral blood lymphocytes are isolated from the patient and a lymphocyte stimulation assay is performed in vitro in the presence of a mitogen and a 5'-nucleotidase resistant inosine-5'-monophosphate. Those patients with a depressed in vitro response to the 5'-nucleotidase resistant inosine-5'-monophosphate are not candidates for treatment with the 5'-nucleotidase resistant inosine-5'-monophosphate.

BRIEF DESCRIPTION OF THE DRAWINGS

Other advantages of the present invention will be readily appreciated as the same becomes better understood by reference to the following detailed description when considered in connection with the accompanying drawings wherein:

FIG. 16 is a line graph comparing the percent survival after aerosol influenza infection and treatments of control (PBS on day –1, —●—), MIMP (100 μg on day –1, —△—), MIMP (100 μg at hour –1, —○—), MIMP (100 μg at hour +1, —◆—), MIMP (200 μg on day –1, —□—), MIMP (200 μg at hour –1, —◊—), and MIMP (200 μg at hour +1, —▽—) and;

FIG. 17 is a line graph comparing the percent survival after aerosol influenza infection and treatments of control (PBS on day –1, —●—), control (PBS at hour +1, —○—), MIMP (200 μg on day –1, —▽—), MIMP (200 μg at hour 1, —△—), MIMP (200 μg plus Squalane on day –1, —◊—), MIMP (200 μg plus Squalane at hour +1, —◆—).

DETAILED DESCRIPTION OF THE PREFERRED EMBODIMENT

Figure 1:
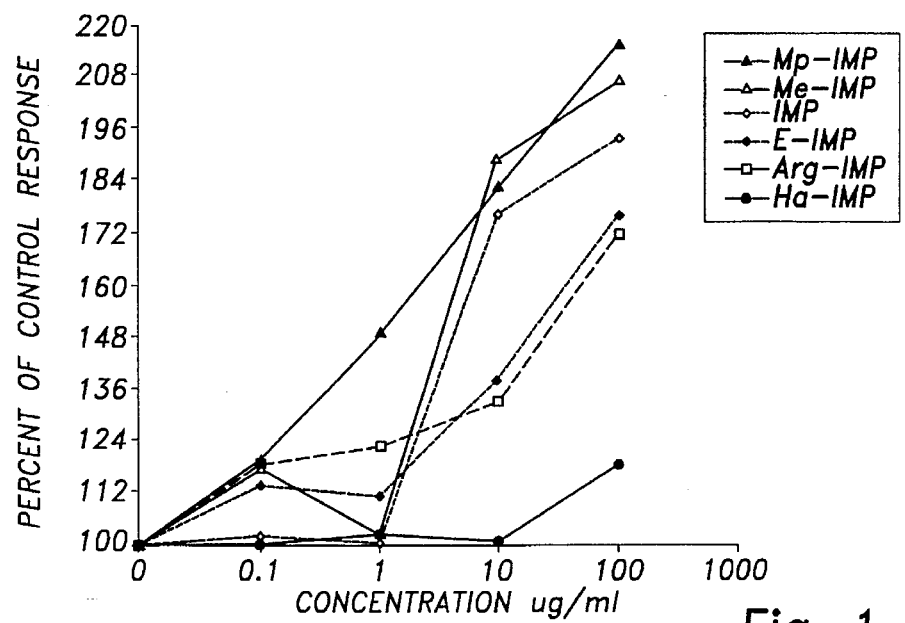
FIG. 1 is a graph plotting the response (i.e., the proliferation of human peripheral blood lymphocytes), as a percent of a control response, of human peripheral blood lymphocytes to the lymphocyte mitogen phytohemagglutinin vs. the dose level of Mp-IMP (—▲—), Me-IMP (—△—), IMP (--◇--), E-IMP (--♦--), Arg-IMP (--□--), and Ha-IMP (—●—) present in the culture medium.

The present invention provides a method of making inosine-5'-monophosphate derivatives that are 5'-nucleotidase resistant (protected-IMP) for use as immunopotentiators. The method provides for chemical modification of inosine-5'-monophosphate or derivatives such that they are 5'-nucleotidase resistant but still retain the biological activity profile of inosine-5'-monophosphate in vitro and extend the biological activity to in vivo uses requiring immunopotentiation/immune stimulation. The methods of preparation are set forth in Preparative Examples 1–5 hereinbelow. In general the chemical method is a condensation reaction between inosine-5'-monophosphate or derivatives and an alcohol, ether or secondary amino compound to form the 5'-nucleotidase resistant compound that is active in vivo.

In still another method of use of the present invention, the protected-IMP can be used to treat tumors, viral infections and intracellular bacterial pathogens. It is unexpected to find a single compound that can act therapeutically in an infected individual to augment the immune response to tumors, pathogens and yet can also act as an adjuvant in vaccination. (The term "therapeutic", as used herein, therefore includes treatment and/or prophylaxis.)

By providing a 5'-nucleotidase resistant compound, protected-IMP, the present invention allows the compound to have an in vivo half-life that is effective in treatments to augment the immune response.

The present invention provides a method of making inosine-5'-monophosphate resistant to 5'-nucleotidase by chemically modifying, as described herein below, inosine-5'-monophosphate to the formula:

[Chemical structure of modified inosine-5'-monophosphate with R—P(=O)(OH)—O— group attached to ribose bearing hypoxanthine base]

wherein R is selected from the group consisting of an alkyl, alkoxy and secondary amino compounds. The alkyl or alkoxy can be from about 1–6 carbon atoms and, in one embodiment, is methyl or a methyl-ester.

The basis of the invention is the protection of inosine-5'-monophosphate (IMP) from hydrolysis by 5'-nucleotidases so that IMP can be used effectively in vivo. In a preferred embodiment, the protected IMP is Methyl-5'-inosine-monophosphate (Methyl-IMP, Me-IMP, MIMP) or methyl-5'-inosine-phosphonate (Mp-IMP). For clarity of discussion, the invention will be disclosed mainly in terms of one of these two embodiments. The invention, however, may be applied in an analogous fashion with any other 5'-nucleotidase protected IMP that has biological activity.

The alkoxy in a 5'-nucleotidase resistant inosine-5'-monophosphate has the formula —OR', wherein R' is an alkyl group of from about 1–6 carbon atoms and in a particular embodiment is a methyl or an ethyl.

The secondary amino compounds in a 5'-nucleotidase resistant inosine-5'-monophosphate includes compounds having the formula $$-\underset{\underset{H}{|}}{N}-R^2,$$

wherein $R^2$ is a substituted normal alkyl group having a total of up to about 16 carbon atoms. The $R^2$ is selected from the group consisting of hydroxyl, amino, carboxyl, secondary-alkyl, alkyl substituted hydroxymethyl, —NHC(NH)NH$_2$, —CONH$_2$,

[phenyl], [4-hydroxyphenyl]—OH, [imidazolyl], and [indolyl]

Preferably, $R^2$ is of the formula $$-\underset{\underset{H}{|}}{\overset{\overset{R^3}{|}}{C}}-(CH_2)_n-R^4$$

wherein $R^3$ is selected from the group consisting of hydrogen, lower $C_1$ to $C_9$ alkyl and carboxyl. In one embodiment, $R^3$ is methyl.

The $R^4$ is selected from the group consisting of hydroxyl, amino, carboxyl, secondary-alkyl, alkyl substituted hydroxymethyl, —NHC(NH)NH$_2$, —CONH$_2$,

[phenyl], [4-hydroxyphenyl]—OH, [imidazolyl], and [indolyl]

and n is an integer of 0 to 4, preferably 1–3 and most preferably 3.

In the embodiment wherein $R^4$ is the secondary alkyl group, it is preferably of the formula —CH($R^5$)$R^6$ wherein $R^5$ and $R^6$, which may be the same or different, are independently selected from alkyl of 1 to 3 carbons. Preferably the secondary alkyl group has a total of 4 carbon atoms.

In the embodiment wherein $R^4$ is the alkyl substituted hydroxymethyl, it is preferably of the formula —C($R^7$)($R^8$)OH wherein $R^7$ and $R^8$, which may be the same or different, are independently selected from hydrogen and alkyl of 1 to 3 carbons where at least one is other than hydrogen. In one embodiment, $R^7$ and $R^8$ are both methyl.

In the 5'-nucleotidase resistant inosine-5'-monophosphate, the secondary amino compound can be a peptide linked through its N-terminal to the phosphorus atom. In one embodiment, the peptide is selected from the group consisting of ARG-PRO, ARG-PRO-LYS and ARG-PRO-LYS-THR. This formula is a preferred embodiment for pharmacologically or immunopharmacologically active peptides wherein eventual hydrolysis will release an active peptide, e.g. tuftsin (ARG-PRO-LYS-THR).

Other suitable active peptides include FK565 (heptanoyl-γ-D-glutamyl-L-mesodiaminopinelyl-D-alanine); Bestatin ([(2S,3R)3-amino-2-hydroxy-4-phenylbutyryl]-L-leucine); Imreg (TYR-GLY); Imreg (TYR-GLY-GLY); $IL_1$ 163–171 (GLN-GLY-GLU-GLU-SER-ASN-ASP-LYS-ILE); Thymulin (Zn: GLU-ALA-LYS-SER-GLN-GLY-GLY-SER-ASN); Thymopentin (ARG-LYS-ASP-VAL-TYR, ARG-LYS-ASP or ARG-LYS-ASP-VAL); and Splenin (ARG-LYS-GLU-VAL-TYR and/or LYS-HIS-GLY).

The protected derivatives of inosine-5'-monophosphate as described herein above may be readily prepared by condensation of a desired alcohol, ether, secondary amino compound including a primary amine or peptide with inosine-5'-monophosphate, preferably in the presence of a condensing agent such as dicyclohexylcarbodiimide or the like. Preparative Examples 1–5 provide examples of such preparations. Suitable alcohols include monohydric alcohols of 1 to 20 carbon atoms such as methyl alcohol, ethyl alcohol, n-propyl alcohol, n-butyl alcohol, n-hexyl alcohol, n-octyl alcohol and n-decyl alcohol.

Suitable primary amines or peptides include 6-amino-2-methyl-2-heptanol (heptaminol), arginine, aspartic acid, asparagine, glutamic acid, glutamine, glycine, histidine, isoleucine, leucine, lysine, phenylalanine, serine, threonine, valine, and ARG-PRO, ARG-PRO-LYS and ARG-PRO-LYS-THR and analogs thereof. Suitable methods of making polyamide-oligonucleotide conjugates are set forth in Haralambidis et al. (1990).

The present invention also provides a method of potentiating the immune response of a mammal in need of treatment of immunogenic stimuli. The method comprises administering to the mammal an immunopotentiating effective amount of a 5'-nucleotidase resistant inosine-5'-monophosphate compound of the formula

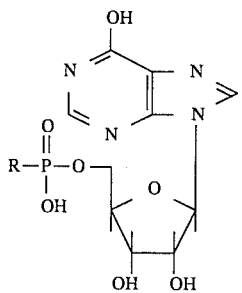

wherein R is a moiety which inhibits hydrolysis of the compound by 5'-nucleotidase and is selected from the group consisting of an alkyl, alkoxy and secondary amino compounds.

More particularly, the present invention provides a method of potentiating the immune response wherein the T-cells are stimulated with an immunopotentiating effective amount of a 5'-nucleotidase resistant inosine-5'-monophosphate compound of the formula:

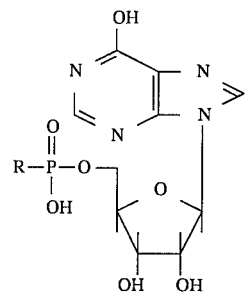

wherein R is a moiety which inhibits hydrolysis of the compound by 5'-nucleotidase and is selected from the group consisting of an alkyl, alkoxy and secondary amino compounds and a pharmaceutically acceptable carrier. In one preferred embodiment, the Th1 T-cell subset are preferentially stimulated.

The protected-IMP of the present invention stimulates the immune system including T-cells. Further, the 5'-nucleotidase resistant inosine-5'-monophosphate derivative can act as an adjuvant in a vaccine to increase response to the other vaccine components. In a preferred embodiment, the vaccine is one for hepatitis B.

The present invention further provides an immunopotentiating composition which comprises an immunopotentiating effective amount of a 5'-nucleotidase resistant inosine-5'-monophosphate compound of the formula:

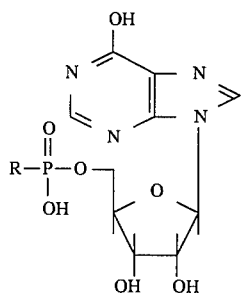

wherein R is a moiety which inhibits hydrolysis of the compound by 5'-nucleotidase and is selected from the group consisting of an alkyl, alkoxy and secondary amino compounds and a pharmaceutically acceptable carrier. In one embodiment, the immunopotentiation is directed to a T-cell immunopotentiating composition and, in a more specific embodiment, to T helper cell subset 1 (Th1) cells.

The present invention also provides for immunopotentiating such that an adjuvant for a vaccine is provided having the formula:

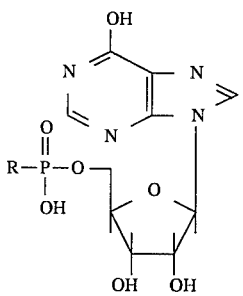

wherein R is a moiety which inhibits hydrolysis of the compound by 5'-nucleotidase and is selected from the group consisting of an alkyl, alkoxy and secondary amino compounds. In preferred embodiments, the alkoxy group has the formula —OR$^1$ and R$^1$ is an alkyl group of from about 1–6 carbon atoms and more particularly methyl and ethyl.

In one embodiment, the present invention is a vaccine for hepatitis B comprising purified viral antigen (preferably recombinant) and an adjuvant for an hepatitis B vaccine having the formula

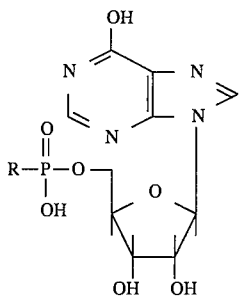

wherein R is a moiety which inhibits hydrolysis of the compound by 5'-nucleotidase and is selected from the group consisting of an alkyl, alkoxy and secondary amino compounds. In preferred embodiments, the alkoxy group has the formula —OR$^1$ and R$^1$ is an alkyl group of from about 1–6 carbon atoms and more particularly methyl and ethyl.

The present invention also provides for the use of 5'-nucleotidase resistant inosine-5'-monophosphate and its derivatives as an immune system stimulator against intracellular bacterial pathogens and viruses having the formula

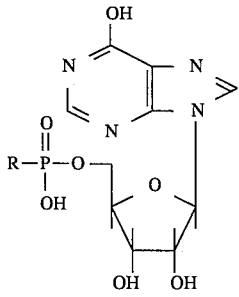

wherein R is selected from either an alkyl group from 1–6 carbon atoms, or an alkoxy group having the formula —OR$^1$, wherein R$^1$ is an alkyl group of from about 1–6 carbon atoms. In selected embodiments, R and R$^1$ is methyl.

The present invention also provides a method for treating viral and intracellular bacterial pathogens in a mammal including the step of diagnosing a patient having an infectious disease caused by a pathogen selected from the group consisting of intracellular bacterial and viral pathogens. The method then provides for administering to the identified patients an effective amount of a protected-IMP (5'-nucleotidase resistant inosine-5'-monophosphate and its derivatives) as an immune system stimulator having the formula

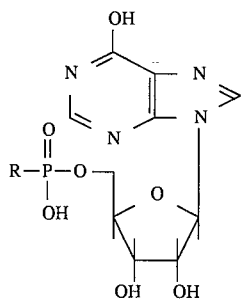

wherein R is selected from either an alkyl group from 1–6 carbon atoms, or an alkoxy group having the formula —OR$^1$, wherein R$^1$ is an alkyl group of from about 1–6 carbon atoms. In selected embodiments, R and R$^1$ is methyl. In a preferred embodiment, an effective amount of Squalane can also be administered and the amount of Squalane administered is 1–5 ml at least daily.

The present invention provides a method of treating tumor bearing patients. The method includes the steps of administering an effective amount of a 5'-nucleotidase resistant inosine-5'-monophosphate as an immune stimulator as described herein and administering an effective amount of endotoxin, such as lipopolysaccharide (LPS) or in a preferred embodiment salmonella vaccine administered as per FDA guidelines. It should be noted that in leukemias it is possible to therapeutically administer an effective amount of a 5'-nucleotidase resistant inosine-5'-monophosphate as an immune stimulator as described herein with the FLV leukemia.

The present invention also provides a method of determining patients who will benefit from treatment with 5'-nucleotidase resistant inosine-5'-monophosphate. The method includes isolating peripheral blood lymphocytes as is known in the art and performing a lymphocyte stimulation assay in vitro in the presence of a mitogen and a protected-IMP. Patients presenting with a depressed in vitro response to the protected-IMP are not candidates for treatment with the protected-IMP.

The terms "immune stimulator" and/or "immunopotentiator", as used herein, refers to compounds which, when administered to an individual or tested in vitro, increase the immune response to an antigen and/or compound in the individual or test system to which it is administered. Some antigens are weakly immunogenic when administered alone or are toxic to the individual at concentrations which evoke immune responses in the individual. The immune stimulator or immunopotentiator may enhance the immune response of the individual to the antigen or compound by making the antigen more immunogenic or may make the immune system more responsive. The immune stimulator/immunopotentiator may also affect the immune response such that a lower dose of the antigen/compound is required to achieve an immune response in the individual.

Intracellular bacterial pathogens include Salmonella, Legionella, Listeria and Brucella. Salmonella species are members of the Enterobacteriaceae. Treatment of viral pathogens contemplated by the present invention include, but are not limited to, influenza, Friend leukemia virus, hepatitis, herpes, and HIV.

For treatment of the diseases discussed herein above, an immune stimulator selected from 5'-nucleotidase resistant inosine 5'-monophosphate derivatives will be given following the diagnosis of a secondary immunodeficiency in conjunction with cancerous tumors, viral infection or intracellular bacterial infection. The immune stimulator will be used at an effective amount and will generally be 1 to 50 mg/kg body weight per day with a preferred embodiment of 1 to 10 mg/kg body weight per day. The immune stimulator will be given at the time of the initial diagnosis, either daily or at times determined in accordance with good medical practice, taking into account the clinical condition of the individual patient, the site and method of administration, scheduling of administration, and other factors known to medical practitioners.

The "effective amount" for purposes herein is thus determined by such considerations as are known in the art of treating secondary immunodeficiencies wherein it must be effective to provide measurable relief in a treated individuals such as exhibiting improvements including, but not limited to, improved survival rate, more rapid recovery, improvement or elimination of symptoms or reduction of post infectious complications and, where appropriate, antibody titer or increased titer against the infectious agent, reduction in tumor mass or other measurements as appropriate and known to those skilled in the medical arts.

In the method of the present invention, the immune stimulator of the present invention, i.e. derivatives of inosine 5'-monophosphate (protected-IMP), can be administered in various ways. It should be noted that the immune stimulator can be administered as the compound or as pharmaceutically acceptable salt and can be administered alone or in combination with pharmaceutically acceptable carriers. The compounds can be administered orally, subcutaneously or parenterally, including intravenous, intraarterial, intramuscular, intraperitoneally, and intranasal administration. Implants of the compounds are also useful. The patient being treated is a warm-blooded animal and, in particular, mammals including man.

It is noted that humans are treated generally longer than the mice exemplified herein, which treatment has a length proportional to the length of the disease process and drug effectiveness. In general doses are proportional to body weight and metabolism and dosages are transferred from animal models exemplified herein to humans taking into account these factors as is known in the art.

The doses may be single doses or, in the preferred embodiment, multiple doses over a period of several days.

When administering the protected-IMP derivatives parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol), propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such as Squalane, cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the protected-IMP derivatives can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

A pharmacological formulation of the protected-IMP derivatives utilized in the present invention can be administered orally to the patient. Conventional methods, such as administering the compounds in tablets, suspensions, solutions, emulsions, capsules, powders, syrups and the like, are usable.

Known techniques which deliver the protected-IMP and its derivatives orally, intravenously or nasally and retain the biological activity are preferred.

In one embodiment, the protected-IMP can be administered initially by intravenous injection to bring blood levels of the protected-IMP to a suitable level. The patient's levels are then maintained by an oral dosage form, although other forms of administration including nasally, dependent upon the patient's condition and as indicated above, can be used. The quantity of protected-IMP and its derivatives to be administered will vary for the patient being treated and will vary from about 10 µg/kg of body weight to 100 mg/kg of body weight per day and preferably will be from 1 to 10 mg/kg per day.

A commercially available FDA approved vaccine can be used to prepare the vaccine-adjuvant combination. Alternatively, a vaccine can be prepared as is known in the art of vaccine preparation. As an exemplar, a hepatitis vaccine is used. For example, a commercially available hepatitis vaccine can be used or one can be prepared with the dosage of hepatitis surface antigen as per FDA guidelines. The adjuvant will be used at a concentration to provide an effective amount and will generally be from 0.01 to 100 mg/kg body weight. In a preferred embodiment, the adjuvant will be used at a concentration to provide 0.01 to 10 mg/kg body weight (Sosa et al., 1992).

Alternatively, a vaccine preparation will be administered and a dose of 5'-nucleotidase resistant inosine-5'-monophosphate derivatives such as Mp-IMP will be co-administered at the same time.

In a further alternative, following the initial administration of the vaccine itself, the co-administration of the vaccine and adjuvant or the combination adjuvant-vaccine, a later administration of the adjuvant can be given. The adjuvant will be used at an effective amount and will generally be at a concentration to provide from 0.01 to 100 mg/kg body weight. In a preferred embodiment, the adjuvant will be used at a concentration to provide 0.01 to 10 mg/kg body weight (Sosa et al., 1992). The adjuvant will be given within seven days of the initial administration, either daily or at times determined in accordance with good medical practice, taking into account the clinical condition of the individual patient, the site and method of administration, scheduling of administration, and other factors known to medical practitioners.

The "effective amount" for purposes herein is thus determined by such considerations as are known in the art of vaccination wherein it must be effective to provide measurable anti-virus titer in persons given the adjuvant and vaccine, and, in a preferred embodiment, persons who are non-responsive to a standard vaccine.

The adjuvant and vaccine can be formulated together in a unit dosage injectable form, or singly, utilizing carriers known in the vaccine art for subcutaneous or parenteral injection including intramuscular and intraperitoneally as well as orally or nasally. The pharmaceutical formulations suitable for injection include sterile aqueous solutions or dispersions and sterile powders for reconstitution into sterile injectable solutions or dispersions. Conventional methods, such as administering the combination adjuvant-vaccine in tablets, suspensions, solutions, emulsions, capsules, powders, syrups and the like, are usable. Known techniques which deliver the present invention orally, nasally, or via injection in which the biological activity is retained are preferred.

To determine if a person who was non-responsive to prior art vaccines and who has been immunized with the present invention is now successfully immunized, titers can be determined, as well as proliferative assays in response to viral antigen can be run as are well known in the art.

Isoprinosine has been shown to have some efficacy in the treatment of lethal influenza challenge in mice; and, when administered with a subinfection dose of virus, it prevented mortality on subsequent challenge with virus (Glasky, 1985). This protective activity is probably explained by the adjuvant activity of isoprinosine.

The activity of 5'-nucleotidase resistant inosine-5'-monophosphate derivatives, as shown in the examples, increase survival and mean survival time in influenza challenge represents activity superior to that of isoprinosine. The use of a 5'-nucleotidase resistant inosine-5'-monophosphate derivative with Squalane to give 100% protection in lethal influenza challenge has not been reported in the prior art for any immunostimulant/immunopotentiator. The effects of a protected-IMP derivative to increase survival and mean survival time after Salmonella and influenza challenge (i.e., therapeutic efficacy) is unique to any IMP that is protected from 5'-nucleotidase. In these infectious challenges, death occurs rapidly and the mechanisms by which the protected-IMP derivative acts are not predicted from its overall immunopharmacologic profile. The action of 5'-nucleotidase resistant inosine-5'-monophosphate derivatives to prolong life and to increase survival in Listeria has not been reported for any other purine immunomodulators.

A hypothesis for the mechanism of immunostimulatory effect of 5'-nucleotidase resistant inosine-5'-monophosphate derivatives can be made, but it is not to be construed as limiting the present invention to this one mode of action. Recent insights into the key mechanisms involved in survival with infectious challenges have been uncovered in studies with facultative intracellular pathogens like Toxoplasma, Leishmania and Listeria (Mossman and Coffman, 1989; Scott, 1991; Haak-Frendocho et al., 1992; Trinchieri, 1993; Tripp et al., 1994, Scott, 1994; Bogdan et al., 1991; Fiorentino et al., 1989). In this model, Th1 cell responses promoted by IL-12 and mediated by IL-2 and γ-IFN and opposed by IL-4 and IL-10 protect animals with infections like Listeria. Th2 responses mediated by IL-4 to IL-10 are associated with lethality with infections like Listeria. This model has been demonstrated to apply to human infections with Mycobacteria leprae (Seiling et al., 1994). It is, therefore, predicted that the 5'-nucleotidase resistant inosine-5'-monophosphate derivatives act by the promotion of Th1 over Th2 responses. This predication is further supported by the preferential action of 5'-nucleotidase resistant inosine-5'-monophosphate derivatives on delayed type hypersensitivity responses over antibody mediated responses (Sosa et al., 1992).

Applicants show in the examples hereinbelow that MIMP is active over a broad concentration range to stimulate the responses of murine and human lymphocytes to a T cell mitogen like PHA and, to a more variable degree, B cell mitogens like LPS and pokeweed. The action of MIMP is further confirmed on responses of enriched human CD4+ and CD8+ lymphocytes. In addition, the results indicate that the suppressive effects of an HIV peptide, IFNα, and $PGE_2$ on the PHA response of normal lymphocytes can be reversed if that suppression is mild to moderate and not extreme or possibly toxic. The results also indicate that the lymphocytes of aged and HIV-infected individuals can respond to stimulation by the protected-IMP in the presence of PHA if the responses are not excessively suppressed. The action of the exemplar Me-IMP in these studies appears to be that of IMP since Me-IMP and IMP action are parallel in vitro.

The preferential action of the 5'-nuclease-resistant-inosine-5'-monophosphate on T lymphocytes implies a receptor based interaction. Me-IMP has been shown to induce differentiation markers of prothymocytes (Touraine et al., 1991) in addition to the effects described herein on mature T lymphocytes.

The purine salvage pathway has important implications for the development and function of T lymphocytes. Deficiencies of both adenosine deaminase and nucleosidephosphorylase result in immunodeficiency syndromes lacking functional T lymphocytes. It can be suggested that some inosine-containing molecule is essential for T lymphocyte development and function. The basis for predicting this lies with transfer factor (Wilson and Fudenberg, 1984). If IMP is part of the transfer factor phenomenon, then protected-IMP can mimic non-specific aspects of transfer factor function, perhaps via a receptor on T lymphocytes. Applicants have confirmed that a transfer factor preparation induces a differentiation marker in prothymocytes, i.e. mimics Me-IMP (Hadden et al., 1986).

The implication that protected-IMP is regulatory for IL-2 action has importance in the central role played by IL-2 in orchestrating cellular immune responses mediated by Th1 type T helper cells. In this regard, it is notable that PEA, the principle mitogen employed in applicants' studies with protected-IMP, elicits preferentially a Th1-pattern of cytokines: IL-1, IL-2, $\gamma$-IFN, and IL-12. Applicants have found that PHA does induce IL-10, but not IL-3 or IL-4. Preliminary data indicate that Mc-IMP has only a small effect on increasing PHA-induced IL-2 or $\gamma$-IFN but potently inhibits IL-10 production. These observations suggest that protected-IMP acts on Th1 responses. Th1 responses have been implicated as critical in the resistance to HIV, cancer, and pathogen infection, i.e., Toxoplasma, Listeria, and Leishmania (Clerici and Shearer, 1995; Teppler, 1993; Scott and Trinchieri, 1989). Thus, effects of protected-IMP to favor these responses implies clinical usefulness in such conditions.

In support of this analysis are the in vivo studies with protected-IMP in which DTH is preferentially stimulated over PFC responses and in which survival has been increased in AIDS, tumor, and infectious challenges (Listeria and Salmonella). In these studies, Me-IMP proved active by the oral route at doses at, or below, 1 mg/kg and was nontoxic (oral $LD_{50}$>5000 mg/kg).

Therefore, clinical applications of protected-IMP compounds such as Me-IMP are relevant to immunorestoration in secondary immunodeficiencies in which T lymphocyte function is compromised, yet T lymphocyte numbers are reasonably preserved. Such deficiencies have been described in the relatively early phases of both HIV infection (ARC) and cancer.

In early HIV infection, T lymphocyte responses have been considered essential to preventing progression to AIDS. T lymphocyte responses are suppressed by products of HIV including gp16O, gp41, and TAT (See Good et al., 1991 for review). Recent work suggests that a retroviral peptide, CKS-17, associated with P-15E, may trigger the Th1 to Th2 shift by inhibiting IL-2 and $\gamma$-IFN production and promoting IL-10 production (Haraguchi et al., 1995). Applicants tested the effect of Me-IMP to reverse the immunosuppressive effect of a 17 amino acid peptide of gp41 having homology for CKS-17 and found reversal if the suppression was mild to moderate. Mc-IMP also augmented PHA responses of HIV-infected individuals. These results indicate that protected-IMP can be employed to inhibit progression of HIV-infected patients to AIDS.

The use of protected-IMP in other viral infections is also disclosed by the present invention since immunosuppression attends viral infections of all types studied (Rouse and Horohov, 1986). Immunosuppression accounts for high mortality of influenza in the elderly and high morbidity due to secondary bacterial infections. Interferon production represents one mechanism by which viruses may suppress immunity. The effect of protected-IMP to reverse the suppression of IFN$\alpha$ on the PHA response recommends its application in this regard.

Inflammation and physical trauma are known to suppress cellular immune responses in part mediated by prostaglandins (Davis and Shires, 1986). The ability of MIMP to reverse the suppressire effect of $PGE_2$ on the PHA response supports its usefulness in these forms of secondary immunodeficiencies.

The above discussion provides a factual and theoretical basis for the use of a 5'-nucleotidase resistant inosine-5'-monophosphate derivatives. The methods used with and the utility of the present invention can be shown by the following examples.

EXAMPLES

General Methods:
Unless otherwise stated, the following materials and procedures were utilized.
Materials:
Methyl-5'-inosine-monophosphate (Methyl-IMP or Me-IMP), methyl-5'-inosine-phosphonate (Mp-IMP), ethyl-5'-inosine-monophosphate (Ethyl-IMP or E-IMP), arginine-5'-inosine-monophosphate (Arginine-IMP or Arg-IMP) and (Heptamin-1-ol)-5'-inosine-monoPhosPhate (Ha-IMP) were prepared as per Preparative Examples 1, 2, 3, 4, and 5, respectively. MIMP preparations for use in cell culture were confirmed to be endotoxin-free by limulus lysate assay (Whittaker Bioproducts, Walkersville, Md.).

Inosine-5'-monophosphate (IMP) and adenosine-5'-monophosphate were obtained from Sigma Chemical Co. (St. Louis, Mo.).

The lymphocyte mitogens phytohemagglutinin (PHA), concanavalin A (Con A) and pokeweed mitogen (PWM) were obtained from Burroughs Wellcome (Research Triangle Park, N.C.), Sigma Chemical (St. Louis, Mo.), Gibco (Grand Island, N.Y.) and Murex Diagnostics (Atlanta, Ga.) as indicated.

Sheep red blood cells (SRBC) were obtained from Diamedix Corp. (Miami, Fla.). Hank's balanced saline and Guinea-pig complement were obtained from Gibco. Agarose was obtained from Bacto (Detroit, Mich.) and DEAE-Dextram from Sigma (St. Louis, Mo.). Tissue culture plates (96 wells and 6 wells) were obtained from Falcon. FICOLL-HYPAQUE was obtained from Pharmacia, Inc. (Piscataway, N.J.) and E. coli lipopolysaccharide (LPS) was obtained from Sigma.

Recombinant IL-2 (rIL-2) was a gift from G. Caspritz of Hoechst Pharmaceuticals (Frankfurt, FRG).

A 17 amino acid sequence from the gp41 portion of the gp16O peptide of the human immunodeficiency virus (HIV) was synthesized and kindly provided to us by M. Strand (Johns Hopkins University, Baltimore, Md.) (Reugg and Strand, 1990).

Prostaglandin $E_2$ was obtained from Sigma Chemicals (St. Louis, Mo.) and recombinant interferon-$\alpha$ (IFN$\alpha$, Intron A) was obtained from Schering Corp. (Kenilworth, N.J.).

The human donors included 22 healthy controls (ages ranging from 20–50), 24 aged individuals (mean age 84 years, ±1), 8 HIV-infected pre-AIDS patients (CDC Class II-mean CD4 count 544), and 8 AIDS patients (mean CD4 count 40).

Human CD4+ and CD8+ lymphocyte subsets were obtained from normal controls using commercial panning techniques (Applied Immune Sciences, Santa Clara, Calif.).
Cell Culture:
All steps relating to cell culture are performed under sterile conditions. General methods of cellular immunology not described herein are performed as generally described in references for cellular immunology techniques such as Mishell and Shiigi, *Selected Methods in Cellular Immunology*, W. H. Freeman & Co., New York (1981) and in Stites and Terr, *Basic and Clinical Immunology*, Seventh Edition, Appleton & Lange (Norwalk, Conn. (1991).
Lymphocyte Transformation
In vitro: Both human peripheral blood lymphocytes (HPBL) and mouse spleen lymphocytes (MSL) were employed. Proliferation was assayed by tritiated thymidine incorporation, as described in Hadden et al. (1975) and Hadden et al. (1986). For HPBL transformation, PHA and PWM were used at 0.5 µg/ml. For MSL transformation, Con A was used at 0.5 µg/ml, phytohemagglutinin (PHA, Murex Diagnostics, Atlanta, Ga.) at 0.5 µg/ml and lipopolysaccharide endotoxin (LPS, Sigma, St. Louis, Mo.) at 10 µg/ml. When protected-IMP derivatives were added, they were added at the onset of culture at varying concentrations ranging from 0.1 µg/ml to 100 µg/ml.

Murine splenocytes were obtained from BALB/c mice, 4–12 months old, by standard procedures (Hadden et al., 1975). They were cultured in microwell plates at $1.5 \times 10^6$ cells/ml of minimal essential media (MEM, Gibco Labs, Grand Island, N.Y.) with 5% fetal calf serum (FCS, Hyclone Labs, Logan, Utah) and tested for their proliferative response to mitogens as measured by incorporation of ($^3$H) tritiated thymidine (New England Nuclear, Wilmington Del., 6.7 µCi/mmol; 2.5 µCi/ml) during a terminal pulse followed by liquid scintillation spectrometry. Human cells were seeded at 104/ml and cultured for 48 hours with an 18 hour pulse with $^3$H-thymidine.

In vivo: Compounds were administered orally, by garage, or intraperitoneally. At termination, spleens were obtained as described in Florentin et al. (1982) and cells were prepared for proliferative response with Con A=0.5 µg/ml, PHA=0.5 µg/ml or LPS=0.5 µg/ml.

Antibody-Forming Cells

Direct mouse spleen antibody-forming cells (PFC) were assayed according to the technique of Jerne et al. (1963) with some modification. Briefly, a group of mice were immunized with SRBC, intraperitoneally, and the compounds of interest were given, orally or intraperitoneally, as indicated in the results. Five days later, suspensions of spleen cells were prepared and their viability was determined by trypan blue exclusion test. Cells were suspended at $3 \times 10^6$/ml. 0.2 ml of spleen cell suspension was mixed with 0.8 ml of 0.7% agarose and 0.2 ml of freshly washed SRBC (at $6 \times 10^5$/ml). The mixture was immediately poured into the plate and allowed to solidify. After 60 minutes of incubation at 37° C. in a humid atmosphere of 5% $CO_2$ in the air, the plate was flooded with 1 ml of guinea-pig complement diluted 1:5 with Hank's balanced saline. Hemolytic plaques were counted with an inverted scope using 4× magnification.

Statistical Analysis

Each experiment was performed from 2 to 10 times as indicated. Quadruplicate samples from each donor at each concentration point were used. Data are expressed as means±standard error of the mean (SEM) for individual representative experiments or as ratio to control±SEM for pooled data. Data were analyzed for statistical significance using Student's t-test, unless otherwise indicated.

Immunoassay Procedures

In general, immunoassays, either EIAs or RIAs, were performed with commercially available kits as indicated. Alternatively, an EIA can be developed as is known to those skilled in the art. Both polyclonal and monoclonal antibodies can be made and used in the assays. Standard antibody production technology is well known to those skilled in the art and is as described generally in Harlow and Lane, *Antibodies: A Laboratory Manual*, Cold Spring Harbor Laboratory, Cold Spring Harbor, N.Y., 1988. Where appropriate, other immunoassays, such as radioimmunoassays (RIA) can be used as are known to those in the art. Available immunoassays are extensively described in the patent and scientific literature. See, for example, U.S. Pat. Nos. 3,791, 932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; and 5,011,771; as well as Sambrook et al., Molecular Cloning: A Laboratory Manual, Cold Springs Harbor, N.Y., 1989.

General Methods for studies with intracellular pathogens:

Depending on the pathogen being tested, different strains of mice were used. To test Salmonella and Listeria BALB/c male mice weighing 14–16 g were used. For responses to influenza virus, the NMRI strain of mice was used. The mice were obtained from the Animal Laboratory, Academy of Medical Science, Russia, and were used in Examples 11–13 set forth herein.

General Methods for studies with Hepatitis Vaccines:

Animals

Different strains of mice, coded by Pre-S2 zone S-gene HBV for their immune responses for proteins place them in the following haplotype order (Benaceraf and McDevitt, 1972): $H-2^b > H-2^d > H-2^s > H-2^k > H-2^f$. DBA/2 mice do not produce antibodies to HBsAg at a high level when treated with antigen alone (Walker et al., 1981). Therefore, male DBA/2 mice weighing 16–18 grams were obtained from the Animal Laboratory, Academy of Medical Science, Russia, and were used in the examples set forth herein. This line of mice was chosen as they are poor responders to hepatitis B vaccine.

Irradiation Protocol

Experimental mice were irradiated at a dose rate of 25 rad/min (1 rad=0.01 Gy) using a $^{60}$Coγ beam source for four minutes. Data represent the average of ten animals in each group.

Immunoassay Procedures

Serum specimens from immunized mice were tested for the presence of anti-HBs in an enzyme immunoassay (EIA) using the diagnostic kits of Roche Diagnostica as per the manufacturer's instructions. The anti-HBs EIA kit (Roche), has a sensitivity of <10 IU/l.

Antibody concentration was determined with the help of calibration curves designed on the basis of the results of anti-HBs detection in standard serum panel (Roche Diagnostica) with the concentrations, as follows: 10 IU/l; 50 IU/l; 100 IU/l and 150 IU/l. The results of the two experiments were used for the calculation of mean values.

Protocol for protected-IMP and HBsAg Administration

HBsAg was administered at a dose of 16 mg/mouse in 0.2 ml PBS (pH 7.4) twice with an interval of two weeks between injections.

A protected-IMP, MIMP, was introduced both orally or intraperitoneally at a dose of 50 mg/kg.

Three schemes of MIMP administration were used:

Scheme #1: MIMP were given orally by garage 30 minutes prior to HBsAG introduction.

Scheme #2: HBsAg and MIMP were given intraperitoneally.

Scheme #3: HBsAg and MIMP were given once intraperitoneally followed by oral administration of MIMP for four days.

Preparative Example 1

Methyl-5'-inosine-monophosphate

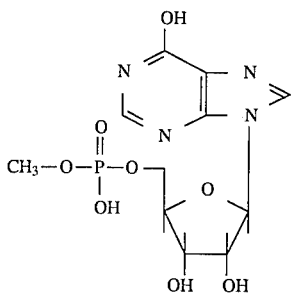

Methyl-5'-inosine-monophosphate was prepared by the reaction of inosine-5'-monophosphate with methanol using dicyclohexylcarbodiimide as a condensing agent.

To a solution of inosine-5'-monophosphate (2.2 mmole) in methanol (300 ml), tributylamine (1.4 ml, 12 mmole), and dicyclohexylcarbodiimide (6.56 g, 30 mmole) are added. The solution was kept four days at 25° C. and evaporated to dryness under reduced pressure. A solution of 2.3% NaOH (20 ml, 11.4 mmole) was added to the residue and the resulting suspension filtered. The precipitate was washed with water (20 ml) and discarded. The filtrate was extracted three times with ether, placed in a column containing 50 g of Amberlite IR/20 PLUS ($NH_4^+$ form) and eluted with water. The UV absorbing fractions were evaporated under reduced pressure and the resulting syrup dissolved in methanol (20 ml). This solution was poured on acetone (300 ml) and the resulting suspension washed with acetone and ether, dried in vacuo over $P_2O_5$ to yield 1.4 g (68%) of a powdery product, m.p. 145° C., UV λ max 249 nm (pH 5.5 $H_2O$) and 253 nm (pH 10).

Anal. Calculated for $C_{11}H_{20}N_5O_9P$ (M.W. 397.24): C, 33.25; H, 5.07; N, 17.63. Found: C, 33.31; H, 5.13; N, 17.34. C, 33.36; H, 5.13; N, 17.34.

NMR data DMSO-$d_6$: 3.50 (s, 3H, $CH_3OP$), 3.20–4.70 (m, 7H, ribose), 5.94 (d, 1H, anomer J-6 Hz), 8.12 (s, 1H, C-2), 8.40 (s, 1H, C-8), 8.20 (br s 5H, NH(CO) and $NH_4$).

Preparative Example 2

Methyl-5'-inosine monophosphonate

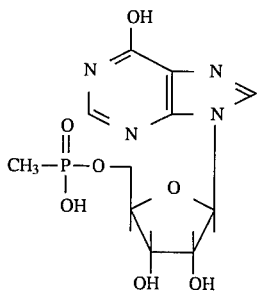

Methyl-5'-inosine monophosphonate was prepared by the reaction of 2',3'-isopropylideneinosine with methylphosphonic dichloride followed by deblocking of the nucleotide.

To a cold mixture of 2',3'-isopropylideneinosine (2 g, 6.49 mmole) in 50 ml of dry pyridine at 10° C. was added methyl phosphonic dichloride (0.86 g, 6.49 mmole) dropwise. After the mixture was stirred for 18 hours, ice and water were added to give the protected nucleotide. Hydrolysis of the blocked nucleotide was effected with formic acid. HPLC was carried out with $H_2O$/methanol. The appropriate fractions were evaporated under reduced pressure to yield methyl-5'-inosine monophosphonate.

Preparative Example 3

Ethyl-5'-inosine-monophosphate

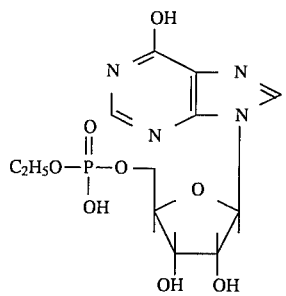

Ethyl-5'-inosine-monophosphate was prepared in a manner similar to Preparative Example 1 except that inosine-5'-monophosphate was reacted with ethanol using dicyclohexylcarbodiimide as a condensing agent.

Preparative Example 4

Arginine-5'-inosine-monophosphate

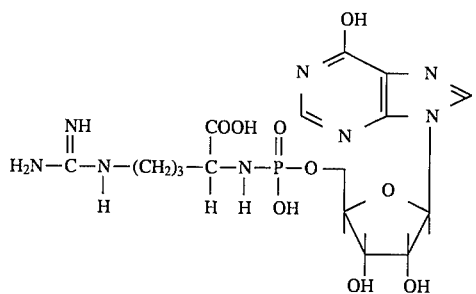

Arginine-5'-inosine monophosphate was prepared by the reaction of inosine-5'-monophosphate with arginine using dicyclohexylcarbodiimide as a condensing agent.

To a solution of inosine-5'-monophosphate (0.55 g, 0.15 mmole) in formamide (3 ml), L-arginine (1.04 g, mmole) base was added. Dicyclohexylcarbodiimide (1.6 g, 7.5 mmole) in t-butyl alcohol (10 ml) was added to the mixture, and the resulting suspension was heated at 80° C. for 8 hours.

The precipitate that was formed was filtered off, washed three times with water, and the combined filtrate evaporated to eliminate the t-butyl alcohol. The solution was extracted three times with equal volumes of ether and evaporated to a syrup in vacuo. Upon addition of ethanol (30 ml), the resulting precipitate was filtered to yield a very hygroscopic gummy material. After standing 10 days, the gummy material became solid, mp 130° C. UV λ max 249 nm ($H_2O$).

Preparative Example 5

(Heptamin-1-ol)-5'-inosine-monophosphate

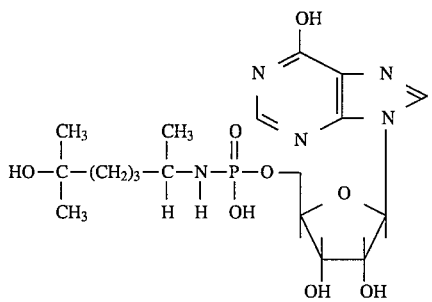

(Heptamin-1-ol)-5'-inosine-monophosphate was prepared by the reaction of inosine-5'-monophosphate with 6-amino-2-methyl-2-heptanol using dicyclohexylcarbodiimide as a condensing agent.

To a solution of inosine-5'-monophosphate monohydrate (1.045 g, 3 mmole) in formamide (5 ml), 6-amino-2-methyl-2-heptanol hydrochloride was added. A solution of dicyclohexylcarbodiimide (6.22 g, 30 mmole) in butyl alcohol (25 ml) was added to the mixture. The resulting reaction mixture was heated, under stirring, at 80°–90° C. for 8 hours. The resulting precipitate was filtered and washed three times with 5 ml water. The precipitate of dicyclohexylurea was discarded, and the combined filtrate was evaporated to eliminate the butyl alcohol. The solution was extracted three times with ether and evaporated to dryness, in vacuo. The oily residue was suspended in acetone to yield a white hygroscopic material. It was purified by dissolution in water and treatment with charcoal, and then precipitated in acetone to yield a white hygroscopic material. UV λ max 249 nm ($H_2O$).

Yield of purified material 0.7 g (53.4%), mp 95° C., having the empirical formula $C_{18}H_{28}N_5O_8P$: % P Calcd. 7.03 Found 5.81.

Preparative Example 6

Hepatitis B virus surface antigen (HBsAg)

Hepatitis B surface antigens (HBsAG; subtype ad and ay) were purified from the blood plasma of antigen carriers according to the following scheme:

(1) HBsAg-containing blood plasma initially diluted with two volumes of physiological saline was heated in a water bath for 60 minutes at 80° C. The clot which formed was removed and mechanically disrupted and the denatured proteins removed by centrifugation.

(2) The HBsAg was then reprecipitated with polyethylene glycol M 6000 at a final concentration of 15% (wt/vol). The HBsAg-containing precipitate was dialyzed against 0.9M NaCl and treated with pepsin (100 mg/ml) and Tween-80 (final concentration—2%).

(3) The resulting HBsAg solution was twice ultracentrifuged in a linear sucrose gradient. The purified HBsAg preparation was dialyzed against 0.9M NaCl, aliquoted in 1 ml volumes and frozen at −60° C.

(4) After 50–100 fold concentration, the resultant preparation had the following characteristics: it consisted only of spherical particles 18–25 nm in diameter and was devoid of DANE particles or filamentous particles of HBsAg. Negative results were obtained in tests for: HBsAg (EIA kit from Abbott Laboratories); DNA-polymerase; HBV-DNA by the method of directed amplification; and the presence of proteins characteristic of normal human blood serum.

The preparation obtained served as the basis for elaboration of experimental lots of hepatitis B vaccine (Alper et al., 1989).

Alternatively, hepatitis B vaccine is available from SmithKline Beecham Biologicals and HBsAG can be purchased from Sigma.

Example 1

Testing of Protection from 5'-nucleotidase Activity

The capacity of 5'-nucleotidase (from Crotalus atrox venom, Sigma Chemical Co. St. Louis, Mo.) to hydrolyze IMP and other compounds was tested by measuring the liberation of inorganic phosphate according to the method of Ames et al. (1960). Nucleotide samples (40–60 nmoles) were incubated at 37° C. for 10 minutes with 0.02 units 5'-nucleotidase in a total volume of 100 µl containing 50 mmoles HEPES, pH 7.3 and 5 mmoles $MgCl_2$. Reactions were terminated by adding 800 µl of 0.42% sodium molybdate in 1N $H_2SO_4$:10% ascorbic acid (6:1, v/v), followed by 0.3 ml $H_2O.KH_2PO_4$; standards 2–80 nmoles) were similarly treated; and samples and standards were incubated at 45° C. for 20 minutes. Phosphate was determined by the absorbance of 820 nm. Blanks consisting of nucleotide but no enzyme were tested in parallel to correct for non-enzymatic hydrolysis. The % hydrolyzed was calculated from the exact amount of nucleotide substrate, determined by ultraviolet absorbance, using the extinction coefficient e=12.2 at 249 nm. The results of four experiments are summarized in Table 1A.

TABLE 1A

Susceptibility of compounds to 5'-nucleotidase attack

| Compound | Hydrolysis (%) |
| --- | --- |
| IMP | 88.0 |
| Me-IMP | 2.1 |
| Mp-IMP | <1.0 |
| E-IMP | 2.9 |
| Ha-IMP | 76.0 |
| Arg-IMP | 12.0 |
| Adenosine MP | 86.0 |

The materials tested were found to be variably resistant to breakdown by 5'-nucleotidase. Ha-IMP and Arg-IMP showed mild and moderate resistance to hydrolysis, respectively, while both Me-IMP and Mp-IMP were extremely resistant to hydrolysis, as was E-IMP. None of the 5'-IMP derivatives was found to inhibit the hydrolysis of IMP, indicating that the compounds are not inhibitors of 5'-nucleotidase, per se.

A further set of experiments was undertaken wherein IMP, MIMP and Adenosine-5'-monophosphate (AMP) were tested for susceptibility to breakdown by 5'-nucleotidase. The protocol was as hereinabove except that the first incubation was for 20 minutes in a total volume of 200 µl, 0.1 mM HEPES and 10 mM $MgCl_2$. The percent hydrolysis of nucleotides was performed in duplicate for each assay. The results are presented in Table 1B.

TABLE 1B

| | Percent hydrolysis by 5'-nucleotidase | | |
|---|---|---|---|
| Compound | Assay 1 | Assay 2 | Assay 3 |
| Me-IMP | 1.5 | 2.2 | 2.6 |
| IMP | 72.0 | 97.0 | 95.2 |
| AMP | 100.0 | 95.1 | 63.7 |

These data indicate that the immunostimulatory effect of 5'-IMP derivatives is a function of the resistance of the substituted 5'-IMP to hydrolysis rather than the nature of the specific substitution.

Example 2

Studies with Human Peripheral Blood Lymphocytes

Response of Normal HPBL to Stimulation by Mitogens

Normal human peripheral blood lymphocytes (HPBL) were stimulated with the mitogenic agents PHA or PWM. In a series of experiments, Ha-IMP, Arg-IMP, E-IMP, Me-IMP, Mp-IMP and inosine-5'-monophosphate (IMP) were analyzed, over a concentration range of 0.1, 1, 10, and 100 μg/ml, for their effect to stimulate these responses. While individual blood donors varied in their responses to these mitogens and to the compounds of interest, all five IMP derivatives consistently stimulated HPBL responses to PHA, as shown in FIG. 1. IMP, per se, showed activity comparable to Me-IMP. Ha-IMP was low, while Arg-IMP, Me-IMP and E-IMP were more active, and Mp-IMP was the most active compound. The compounds tested showed little or no effect on the PWM response. None of the compounds stimulated HPBL in the absence of mitogen. Since the PHA response reflects T-lymphocyte proliferation and the PWM response reflects B-lymphocyte proliferation, the results indicate that the 5'-substituted IMP derivatives preferentially potentiate T-lymphocyte responses. As an exemplar Me-IMP (MIMP) is used in the following experiments.

Figure 2:
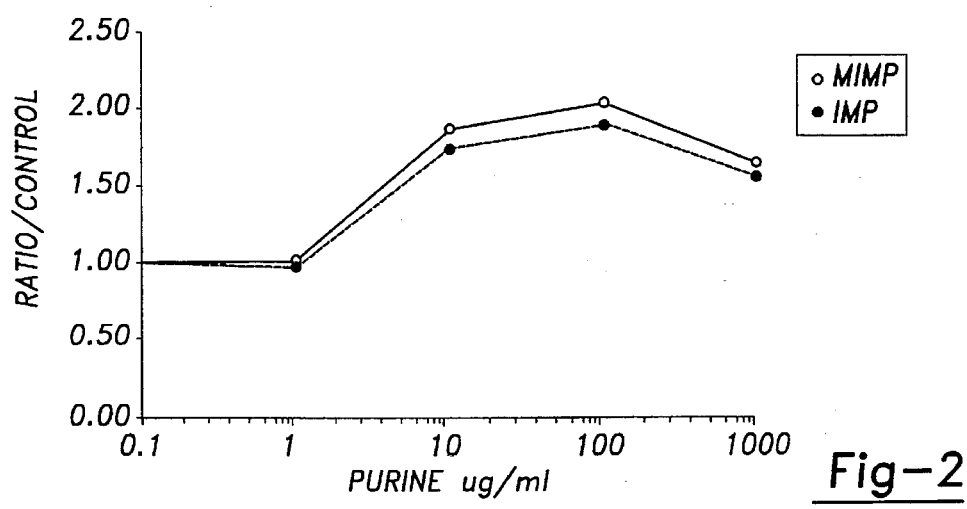
FIG. 2 is a graph plotting the dose response curve of normal human lymphocytes to MIMP (—○—) and IMP (--●--), from 1 to 1000 μg/ml in the presence of 0.5 μg/ml PHA with the results expressed as the ratio to the control of 2 donors.

In FIG. 2 the results of HPBL responses to PHA in vitro of two donors in the presence of IMP and MIMP are presented. The responses of control lymphocytes for three normal donors to stimulation with PWM again were not affected by MIMP over a range of concentrations.

Figure 3:
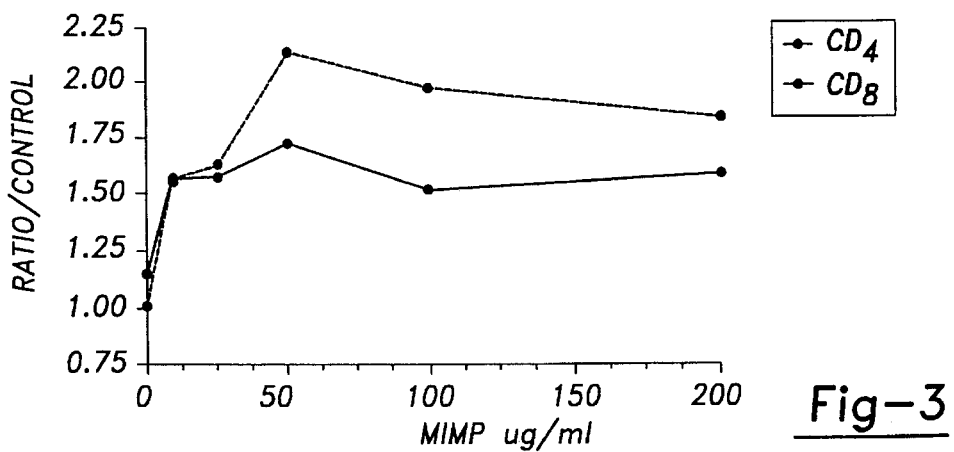
FIG. 3 is a graph plotting the dose response curve of $CD4^+$ (—○—) and $CD8^+$ (--●--) enriched control human lymphocytes from 3 donors to MIMP (1–200 μg/ml) in the presence of PHA.

Human peripheral blood lymphocytes are on average approximately 80% T lymphocytes and 20% B lymphocytes and of the T lymphocytes, ⅔ are of the CD4+ helper/inducer phenotype and ⅓ are the CD8+ suppressor/cytotoxic phenotype. Enrichment of CD4+ T cells or CD8+ T cells can be achieved through reduction of the other phenotype (>98%) removal using adherence to monoclonal antibody-coated flasks (panning). Such enrichment was employed with three normal controls (pooled data) and FIG. 3 shows the effect of MIMP on these two cell populations. The PHA responses of CD4+ and CD8+ lymphocytes are significantly augmented by MIMP ($p < 0.01$ for the response of each of the three individuals).

Figure 4:
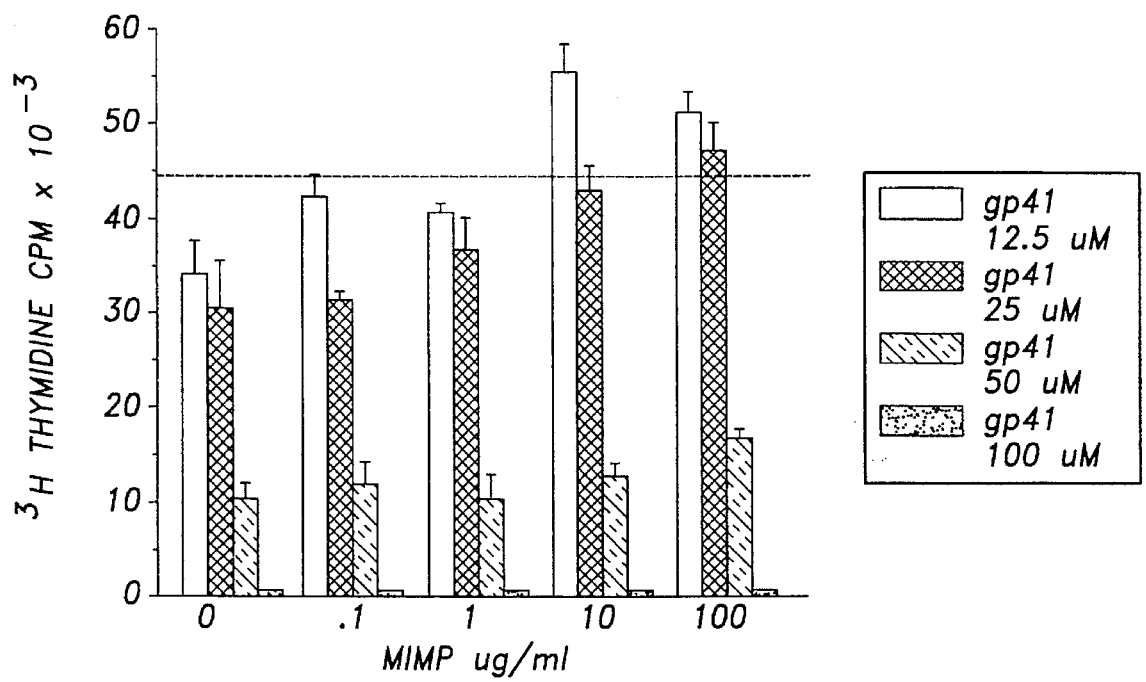
FIG. 4 is a bar graph of the dose response of control human lymphocytes to peptide gp41 at 12.5 μM (open bar), 25 μM (cross-hatched bar), 50 μM (solid bar), and 100 μM (stippled, shortest bar) in the presence of varying concentrations of MIMP (0.1–100 μg/ml), the control value without peptide is indicated by the horizontal --- line and the results represent the CPM±SEM of one representative donor of the 5 tested.

Responses of HBPL to Suppression by an HIV-derived Peptide, Interferon α and $PGE_2$ A synthetic 17 amino acid peptide representing the immunosuppressive site of the intramembranous gp41 portion of the human immunodeficiency virus (HIV) was tested on lymphocytes from controls. One representative experiment of five is shown in FIG. 4 in which this peptide induced progressive inhibition of PHA-induced lymphocyte proliferation with a maximally suppressive dose of 100 mM. The effect of MIMP from 0.1–100 μg/ml was examined in combination with varying degrees of inhibition by the peptide. MIMP restored the proliferative responses to near-normal ranges when the peptide-induced suppression was less than 50%; however, when the inhibition was more severe (>50%), MIMP's effect was not significant. These data indicate that MIMP is able to reverse the immunosuppressive effect of HIV-associated peptide when the effect is mild to moderate but not when it is severe.

Figure 5:
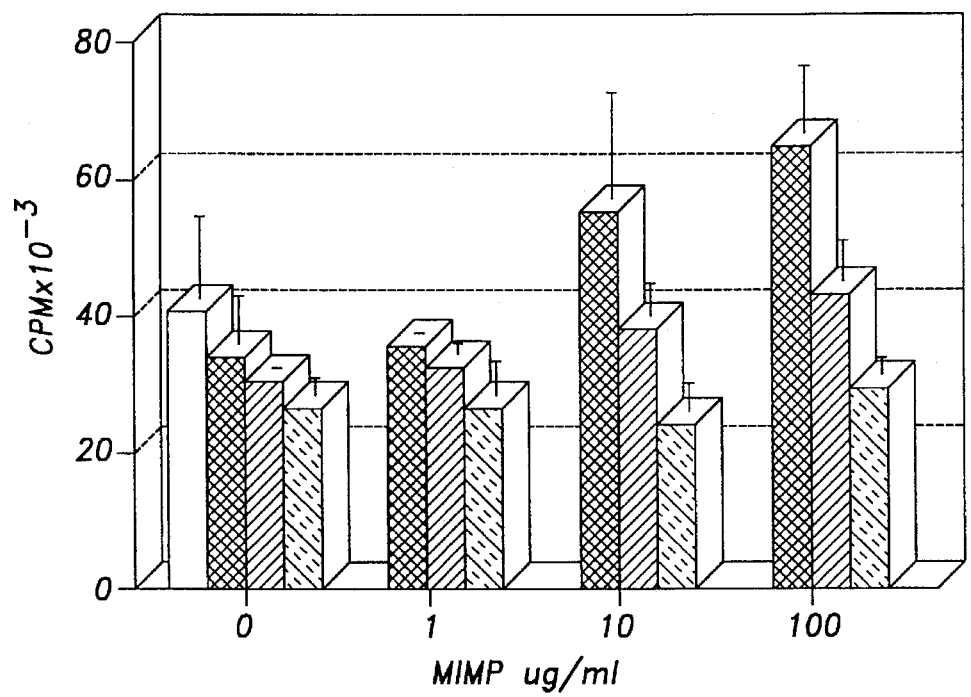
FIG. 5 is a bar graph of the dose response of control human lymphocytes to the suppressive influence of recombinant interferon α at 10 (cross-hatched bar), 100 (diagonal), and 1000 (solid) units/ml in the presence of MIMP 1–100 μg/ml, control (open bar) is the response to PHA alone, and the results are expressed as CPM±SEM.

Virus infections are associated with depressed lymphoproliferative responses. FIG. 5 shows the effect of a virus-induced mediator, rIFN-α to inhibit the in vitro PHA-response of lymphocytes from controls and the effect of MIMP at 1, 10, 100 μg/ml to reverse the inhibition when it is moderate, i.e. at the concentration of 10 and 100 units/ml IFN α.

Figure 6:
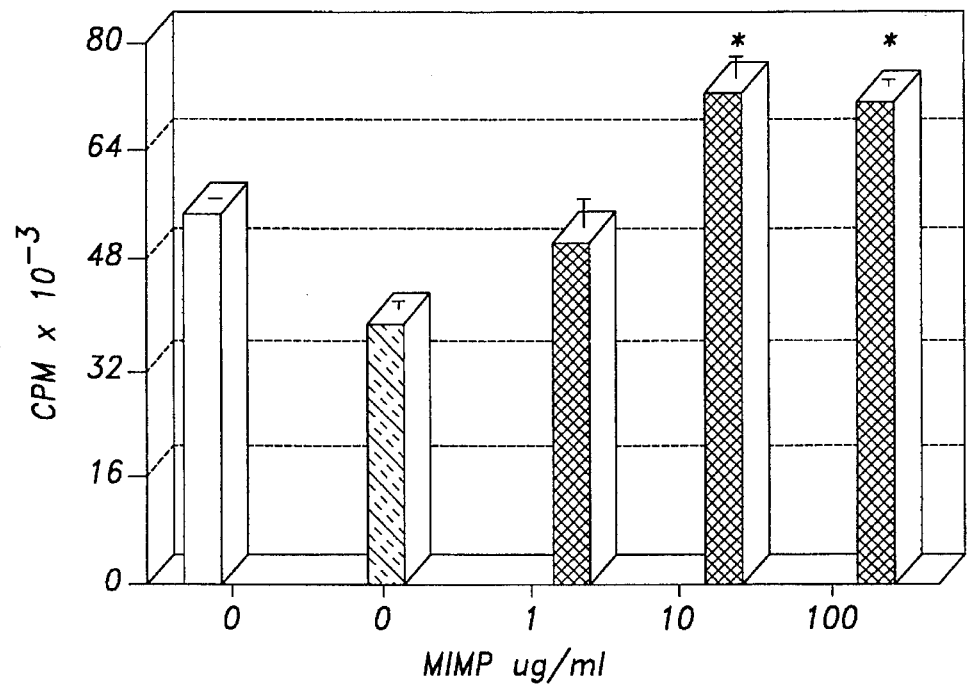
FIG. 6 is a bar graph of the effect of $PGE_2$ ($10^{-5}$M) to inhibit (solid bar) the proliferative response of control human lymphocytes and the effect of MIMP at 1, 10 and 100 μg/ml to reverse this inhibition (cross-hatched), control (open bar) is PHA response in the absence of MIMP, data are expressed as CPM±SEM.

Inflammation, as seen in rheumatoid arthritis, is associated with depressed lympho proliferative responses. FIG. 6 shows the effect of one inflammatory mediator, $PGE_2$ (at $10^{-5}$M), to inhibit the PHA response of normal lymphocytes and the effect of MIMP (1–100 μg/ml) to reverse the inhibition.

Responses of HPBL from Aged and HIV-infected Individuals

Figure 7:
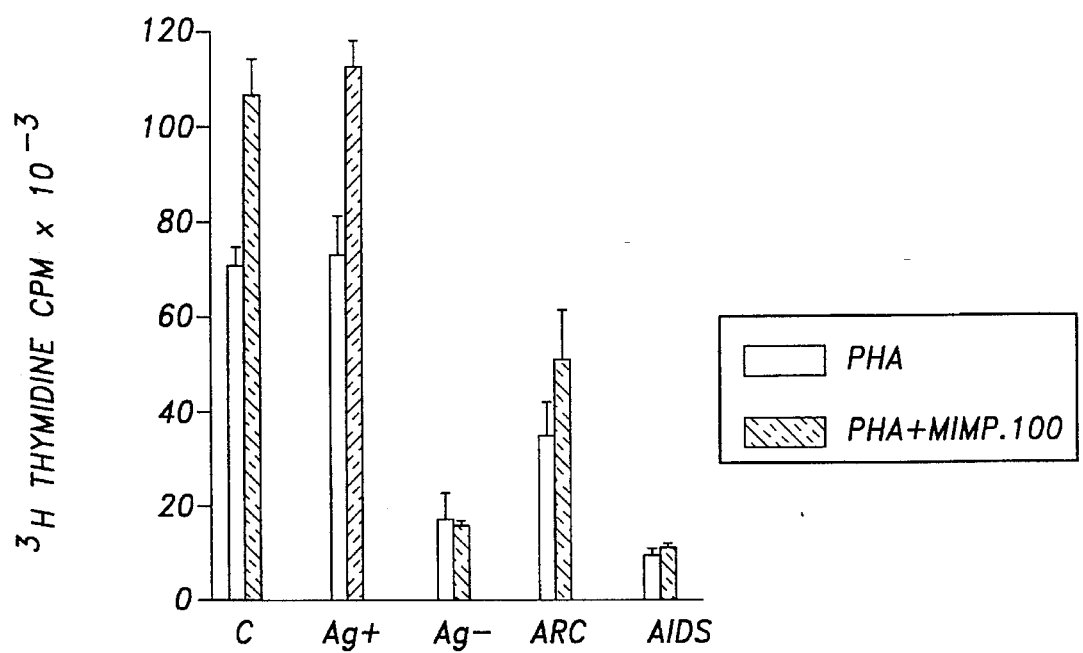
FIG. 7 is a bar graph of the effect of MIMP at 100 μg/ml (solid bar) on the PHA response (open bar) of controls (c), 15 normal aged individuals (Ag+), 9 aged individuals with depressed PHA responses (Ag–), 8 ARC patients and 8 AIDS patients.

FIG. 7 depicts the PHA responses of these aged and HIV-infected individuals and the effect of stimulation with 100 μg/ml of MIMP compared to normal controls (C). The control patients (22) had normal PHA and MIMP responses. Fifteen aged patients (Ag+) had normal PHA responses and responses to MIMP. Nine aged patients (Ag−) had markedly depressed responses to PHA and also to MIMP. Of the nine apparently healthy aged patients who showed a poor response to PHA, five were tested for lymphocyte counts and were on average normal.

Eight HIV-infected (ARC) individuals averaged 50% of the mean normal PHA responses and showed a significant response to MIMP. Eight AIDS patients showed no response. These data suggest that clinical subjects for MIMP treatment should be pretested to sensitivity to the drug in vitro prior to treatment.

The above experimental protocol was repeated with Mp-IMP at 10 and 100 μg/ml with the same results as seen with 100 μg/ml MIMP.

Example 3

STUDIES WITH MURINE SPLENIC LYMPHOCYTES

Figure 8:
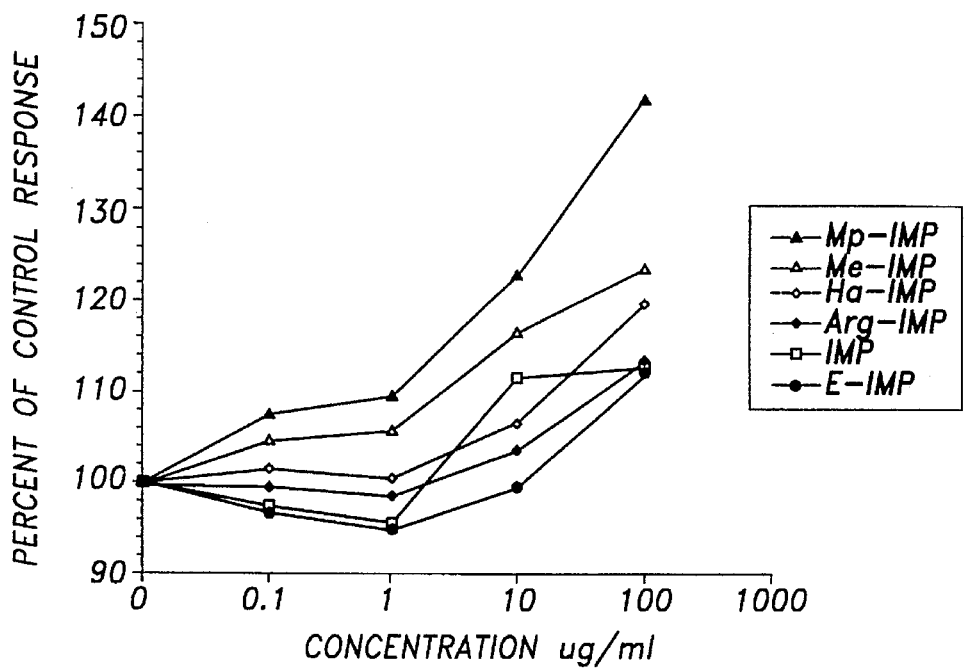
FIG. 8 is a graph plotting the response (i.e. the proliferation of mouse spleen lymphocytes), as a percent of a control response, of mouse spleen lymphocytes to the lymphocyte mitogen concanavalin A vs. the dose level of IMP (--□--), Me-IMP (—△—), E-IMP (—●—), Arg-IMP (--♦--), Ha-IMP (--◇--) and Mp-IMP (—▲—) present in the culture medium.

MSL were stimulated with the mitogenic agents Con A and LPS. Ha-IMP, Arg-IMP, E-IMP, Me-IMP, Mp-IMP and IMP were analyzed in a series of experiments over a concentration range of 0.1, 1, 10 and 100 μg/ml for their effect to stimulate these responses. Ha-IMP, Arg-IMP, E-IMP, Me-IMP, Mp-IMP and IMP stimulated the proliferative responses of MSL to Con A, as shown in FIG. 8.

Comparing the mouse (FIG. 8) and human lymphocyte (FIG. 1) data, human tymphocytes are more sensitive to these compounds than mouse lymphocytes.

In a further experiment, murine splenocytes were incubated with PHA or LPS and MIMP (1–100 μg/ml). MIMP did not affect splenocyte responses in the absence of mitogens. In the presence of mitogens, MIMP progressively and significantly augumented the proliferative responses of lymphocytes as measured by tritiated thymidine incorporation as shown hereinbelow. Splenocyte responses to PHA preferentially reflect T lymphocyte responses, confirming the responses seen with ConA. The LPS responses also parallel the previous experiment.

| MIMP µg/ml | PHA 0.5 µg/ml | LPS 10 µg/ml |
|---|---|---|
| 0 | 100933 ± 4202 | 44864 ± 2350 |
| 1 | 106647 ± 4917 | 47261 ± 997 |
| 10 | 117247 ± 6500* | 57481 ± 2343* |
| 100 | 124801 ± 6630** | 55153 ± 6176* |

The data was obtained from four different animals and represent quadruplicate samples for each concentration. They are expressed as mean CPM±SEM, with * showing a significance of $p<0.05$ and ** showing $p<0.01$.

Example 4

In vivo Stimulation of PFC Response

Intraperioneally (ip) Administered

Figure 9:
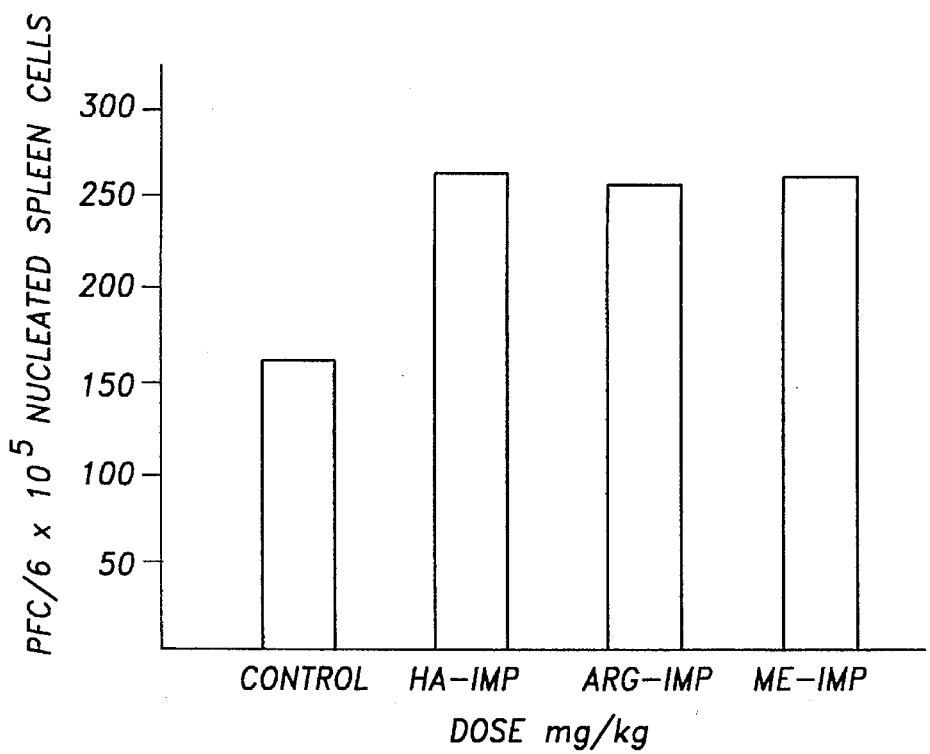
FIG. 9 is a bar graph plotting the number of spleen plaque antibody forming cells (PFC) formed (mean±SEM) when spleen cells harvested from mice, which have been immunized against sheep red blood cells (SRBC), are challenged with SRBC where immunization of the mice was conducted in conjunction with intraperitoneal administration of Ha-IMP, Arg-IMP, Me-IMP.

To determine whether the compounds stimulate lymphocytes, in vivo, mice were immunized with sheep erythrocytes (SRBC), $1 \times 10^8$ cells, and 50 mg/kg of body weight of Ha-IMP, Arg-IMP, Me-IMP or IMP, ip, and spleen plaque antibody forming cells (PFC) were measured five days later. Ha-IMP, Arg-IMP and Me-IMP significantly stimulated the PFC response (as shown in FIG. 9). IMP was compared to control in three experiments at 50 mg/kg body weight and had no significant effect (IMP: 12 samples with mean PFC 197±21; control: 15 samples with mean PFC 210±17). This shows that IMP only has activity in vivo when protected from 5'-nucleotidase activity.

Figure 10A:
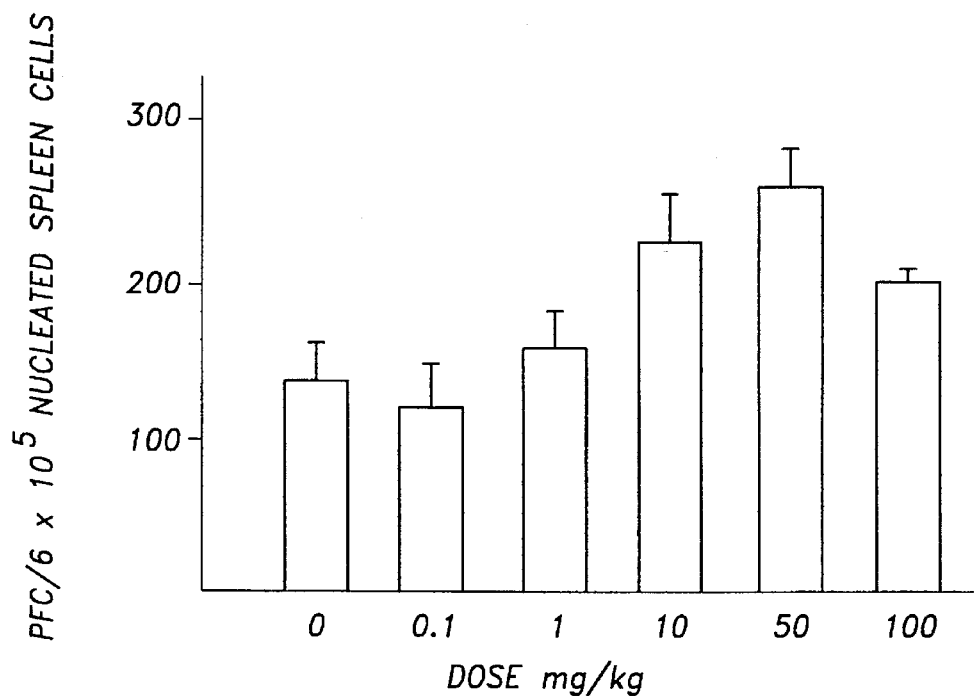
FIGS. 10A–C is a dose response bar graph plotting the number of spleen PFC (mean±SEM) formed when spleen cells harvested from mice, which have been immunized against SRBC, are challenged with SRBC, where immunization of the mice was conducted in conjunction with intraperitoneal administration of various doses of (A) (heptamin-1-ol)-5'-inosine-monophosphate (B) arginine-5'-inosine-monophosphate and (C) methyl-5'-inosine-monophosphate.
Figure 10B:
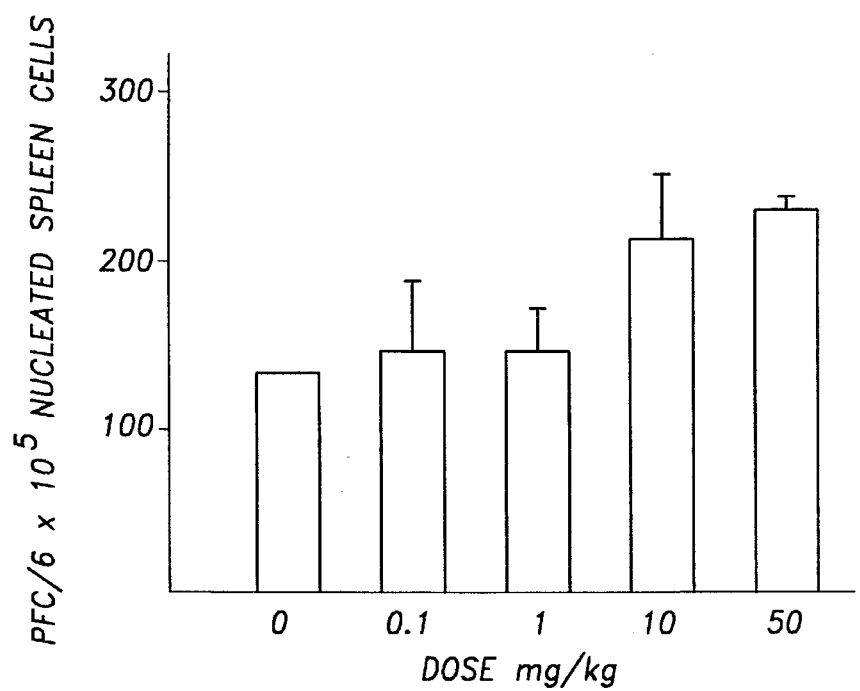
Figure 10C:
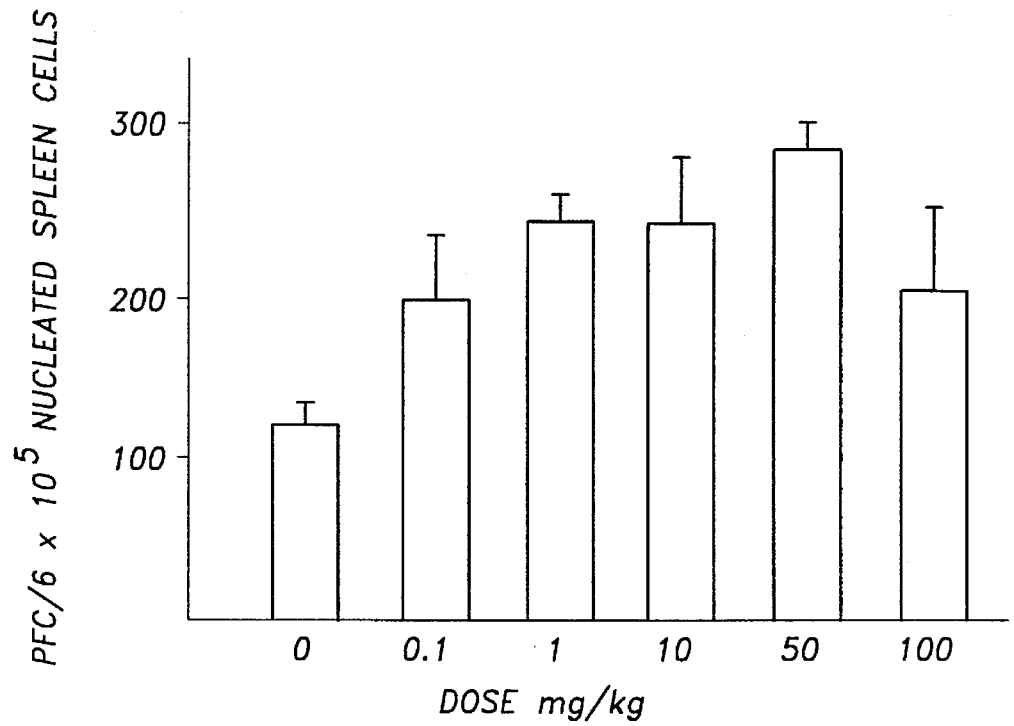

Dose response data for Ha-IMP, Arg-IMP and Me-IMP on the PFC response were developed as shown in FIG. 10A, 10B and 10C, respectively. All three compounds stimulated optimally at 50 mg/kg of body weight; however, Me-IMP was active at lower doses.

In contrast, in the in vitro data with mouse lymphocyte proliferation, Me-IMP appeared to be the most potent of the compounds tested.

Oral Administration

Figure 11:
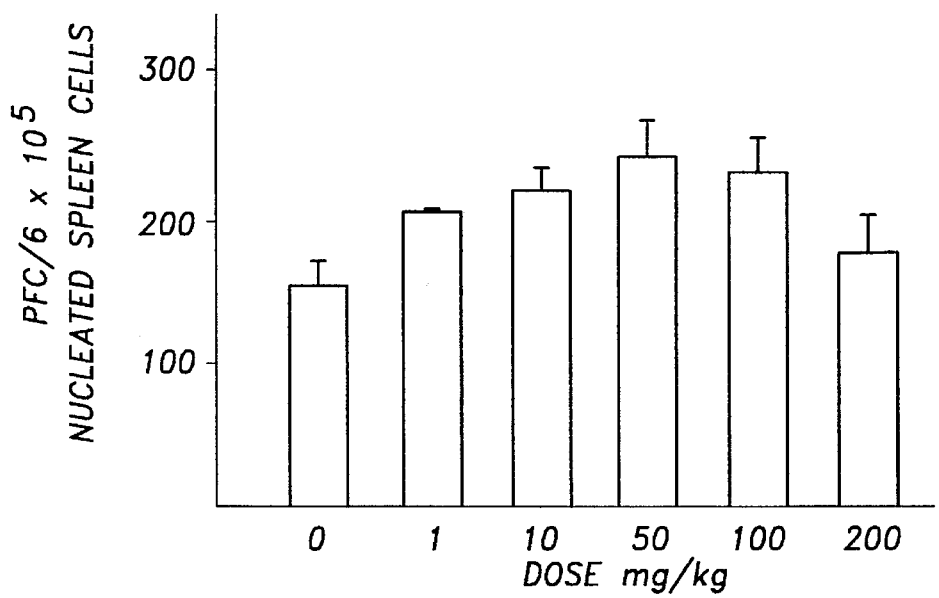
FIG. 11 is a dose response bar graph plotting the number of spleen PFC (mean±SEM) formed when spleen cells harvested from mice, which have been immunized against SRBC, are challenged with SRBC, where immunization of the mice was conducted in conjunction with oral administration of various doses of methyl-5'-inosine-monophosphate.

To determine whether there is activity upon oral administration, mice were immunized with sheep erythrocytes (SRBC), $1 \times 10^8$ cells, intraperitoneally, and orally with Me-IMP. The Me-IMP was administered at the time of immunization with the SRBC antigen and daily for five days thereafter. Spleen plaque antibody forming cells (PFC) were measured at the end of the five days. FIG. 11 shows the results for various dose levels of the Me-IMP.

Multiple doses of Me-IMP given orally with the SRBC antigen and daily for five days stimulates the PFC response with a peak at 50 mg/kg of body weight.

Example 5

In vitro Response to Mitogens Following In vivo Administration of Me-IMP

A parallel experiment to that of Example 4 confirms that both the PHA and Con A responses of spleen lymphocytes are stimulated by oral administration of Me-IMP.

Figure 12:
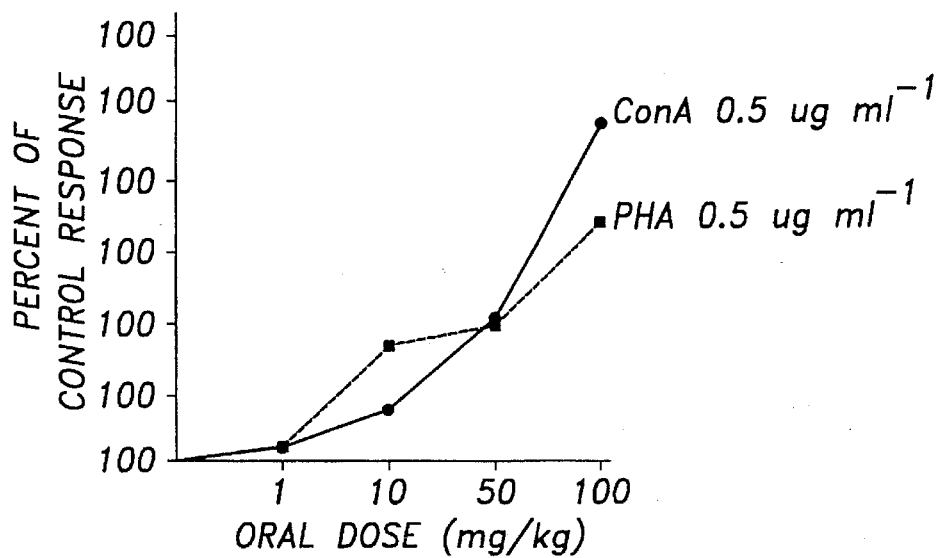
FIG. 12 is a graph plotting the response (i.e., the proliferation of mouse spleen lymphocytes), as a percent of a control response, of mouse spleen lymphocytes to the lymphocyte mitogens phytohemagglutinin (--■--) and concanavalin A (--●--) vs. the dose level of methyl-5'-inosine-monophosphate.

Spleen lymphocytes were obtained from mice that had been orally administered Me-IMP for five days, range of 0–100 mg/kg body weight, and then sacrificed. The spleen lymphocytes were incubated with PHA (0.5 µg/ml) or Con A (0.5 µg/ml) for 48 hours. Cultures were pulsed with tritiated thymidine for the last 18 hours. FIG. 12 shows the results for various oral dose levels of the Me-IMP.

These data indicate that the 5'-IMP derivatives, in contrast to IMP, are potent adjuvants for a T-cell-dependent antibody response and, in the case of Me-IMP, a potent stimulant of T-lymphocyte proliferative responses.

At the doses utilized, the Me-IMP was both parenterally and orally active and apparently non-toxic. The acute toxicity (LD50) of Me-IMP was greater than 500 mg/kg of body weight, intraperitoneally, and greater than 5000 mg/kg of body weight, orally.

Example 6

Stimulation of Delayed-Type Hypersensitivity In vivo

Mice were immunized by intraperitoneal administration of SRBC in graded doses of from $10^6$ to $10^9$ cells. Preliminary experiments indicated that an optimum immunizing dose of SRBC for delayed-type hypersensitivity was between $10^7$ and $10^8$ cells. A dose of $10^7$ was chosen to immunize animals in this study.

Four days following immunization, each mouse was challenged by injecting the left hind footpad subcutaneously with $10^8$ SRBC in 50 µl phosphate buffered saline (PBS). Vehicle (50 µl PBS) was injected subcutaneously into the right hind footpad as a control. The compounds being tested were injected intraperitoneally either at the time of immunization or at the time of elicitation. After 24 hours of challenge, footpad swelling was measured as the increase in footpad thickness (left minus right) using Engineer's calipers.

Figure 13:
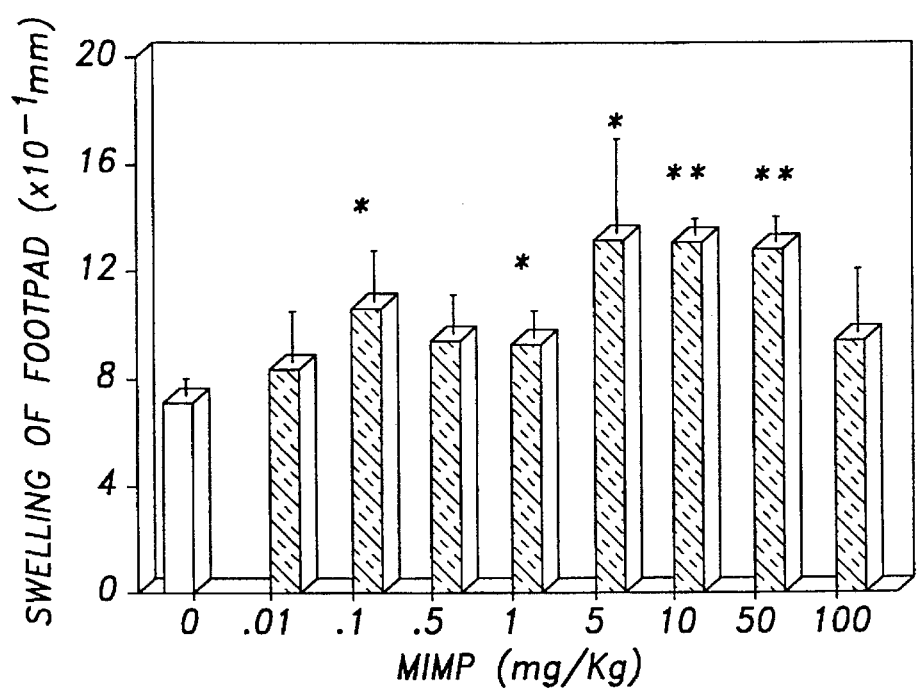
FIG. 13 is a dose response bar graph plotting the delayed-type hypersensitivity response (i.e., the mean footpad thickness increment±SEM) upon challenge vs. the dose level of methyl-5'-inosine-monophosphage administered at the time of immunization.
Figure 14:
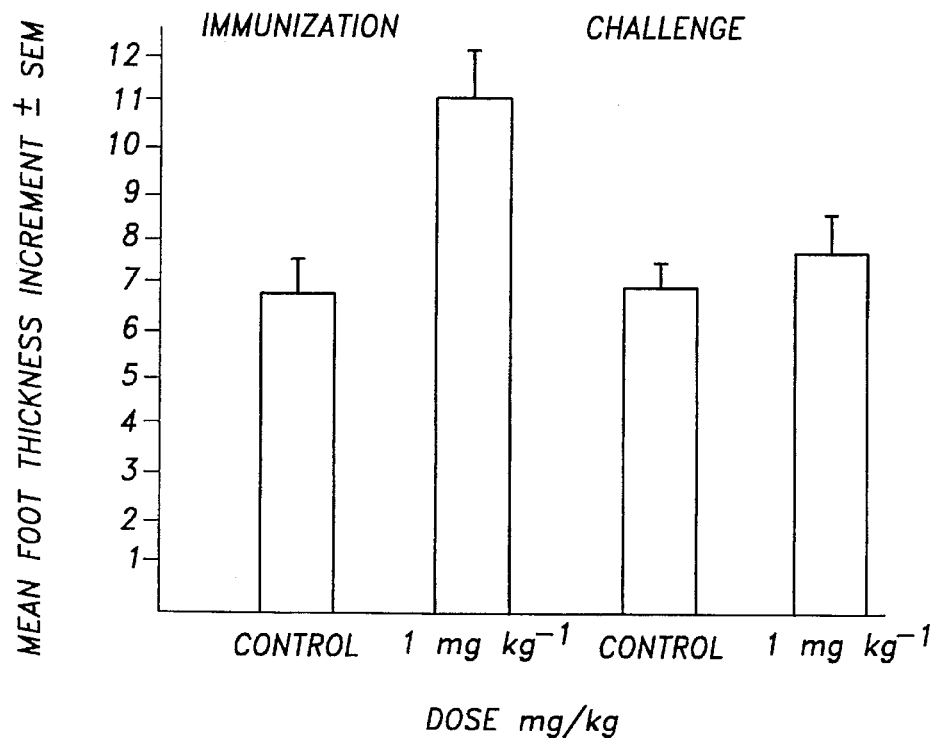
FIG. 14 is a bar graph comparing the delayed-type hypersensitivity response (i.e, the mean footpad thickness increment±SEM), upon challenge for administration of control or methyl-5'-inosine monophosphate (Mc-IMP), at the time of immunization with administration of control and Me-IMP at the time of challenge.

The results are expressed as increments of footpad thickness in 0.1 mmunits. The characteristics of delayed-type hypersensitivity measured in this way have been described previously in MacDonald et al. (1979). FIGS. 13 and 14 show the results of this testing. In particular, FIG. 13 shows a dose-response plot for Me-IMP when administered at the time of immunization. FIG. 14 shows the response for Me-IMP when administered at the time of immunization (Immunization) and when administered at the time of challenge (Challenge).

When the Me-IMP was administered as one dose at the time of immunization, it significantly stimulated the delayed-type hypersensitivity response. When the Me-IMP was administered as one dose at the time of challenge, its effect was not significant. These data indicate that Me-IMP promotes cellular immunity, presumably through an action on the afferent limb of the immune response, T helper cells. It does so at lower doses than those augmenting antibody production indicating a preferential effect on DTH and, therefore, Th1 cells, which mediate this response.

Example 7

In vivo Treatment By Protected-IMP Derivatives

Friend's Leukemia Virus (FLV)

Figure 15:
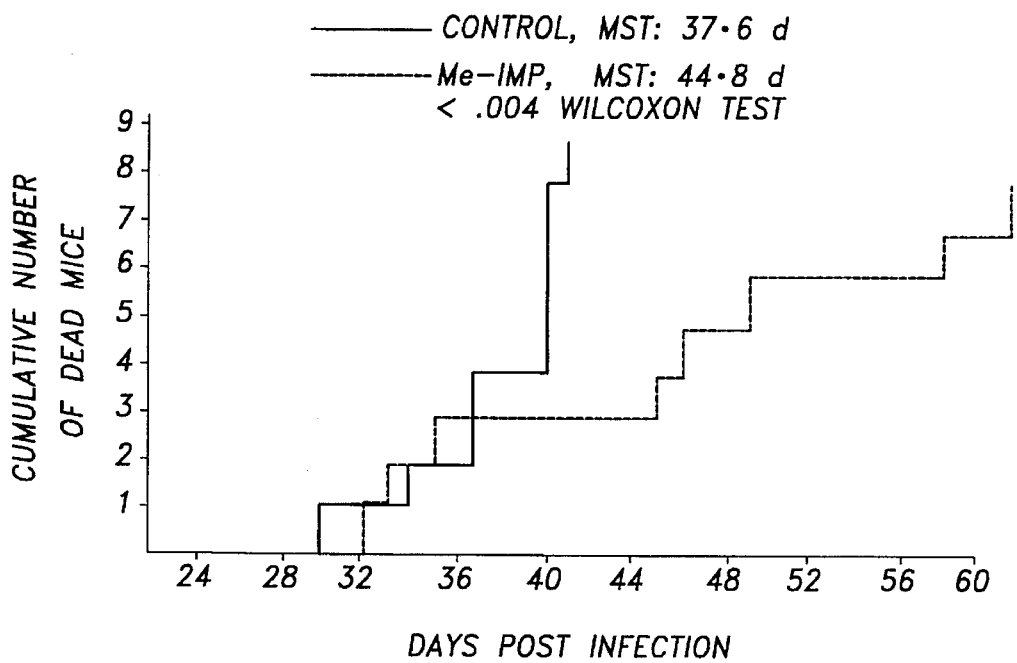
FIG. 15 is a line graph comparing the survival of control (—) and Me-IMP (---) treated mice infected with Friend Leukemia Virus (FLV)

To demonstrate clinical usefulness of immunodulatory protected-IMP derivatives, BALB/c mice were infected with Friend Leukemia Virus (FLV). Control mice were treated with saline intraperitoneally from day 3 to day 13 following infection, and Me-IMP treated mice were treated with 1 mg/kg/day from day 3 to day 13, and the day of death was recorded. FIG. 15 shows that Me-IMP treated mice had a larger mean survival time (MST) which was statistically significant (P<0.004) by Wilcoxon test.

Tumor-bearing

In order to test the effect of Me-IMP on cancer-bearing animals, groups of swiss mice (6) were inoculated subcutaneously with Meth A tumor, according to the method of Carswell et al. (1975). After 8 days, when the tumors were approximately 8 mm in size, the animals were treated intravenously with a priming dose of various amounts of Me-IMP or an equal volume of saline. Five hours later the animals were treated intravenously with 10 μg of lipopolysaccharide endotoxin (LPS). Tumor necrosis factor (TNF) levels were analyzed in serum at 24 hours and tumor necrosis (− to +++) was evaluated at 48 hours after treatment. Complete tumor regression was evaluated on day 20. Results are shown in Table 2.

TABLE 2

| Treatment Table | | Tumor | | | | | |
|---|---|---|---|---|---|---|---|
| Primary | Eliciting | Tumor Necrosis | | | | Regression | Alive |
| (μg) | (μg) | +++ | ++ | + | − | No/Total  % | Day 20 |
| MeIMP (1000) | LPS (10) | 5 | 1 | 0 | 0 | 1/6  16.7 | — |
| MeIMP (100) | LPS (10) | 2 | 6 | 1 | 3 | 2/12  16.7 | 6/6 |
| MeIMP (10) | LPS (10) | 1 | 3 | 1 | 1 | 1/6  16.7 | — |
| MeIMP (100) | Saline | 0 | 0 | 0 | 6 | 0/6  0 | — |
| Saline | LPS (10) | 0 | 0 | 2 | 4 | 0/6  0 | 0/6 |

Table 2 shows that while Me-IMP (100) alone, or LPS (10) alone, had no significant effect on tumor necrosis (all + or −), tumor regression (0/12) or survival time past 20 days (0/6), Me-IMP (100) plus LPS (10) induced significant tumor necrosis (2/3 were ++ or +++), complete tumor regression (2/12) and increased survival at 20 days (6/6). Under these condition, TNF levels were greater at 24 hours in Me-IMP treated plus LPS (4 mice) than saline plus LPS (4 mice) controls (4240 vs. <200). These data indicate that Me-IMP, when used with LPS but not alone, has significant anticancer activity, presumably mediated by the induction of TNF and related lymphokines.

Example 8

Effect of a Protected-IMP On Listeria Infection

Protocol:

Infection. A mouse-adapted bacterial strain *L. monocytogenes* EGD (Gamaleya Research Institute Academy Medical Science, Russia) was administered to male BALB/c mice (14–16 μm) in a dose of $1.7 \times 10^4$ cells/mouse i.p. in 0.5 ml PBS (pH=7.4) on Day 0.

Treatment. Solutions with various concentrations of MIMP (AGS-36-217) were administered either orally or parenterally as shown in Table 3 starting 5 days prior to infection (Day—5).

TABLE 3

DIFFERENT TREATMENT FOR ANTIINFECTIONS PROTECTION (*L. monocytogenes*)

| Scheme | MIMP Dose | Route | Number of Doses | Treatment Start Days Prior to Infection (Day 0) |
|---|---|---|---|---|
| N1 1 | 0.1 | per os | 1 | Day −5 |
| 2 | 1.0 | per os | 1 | Day −5 |
| 3 | 10.0 | per os | 1 | Day −5 |
| N2 4 | 0.1 | i.p. | 1 | Day −5 |
| 5 | 1.0 | i.p. | 1 | Day −5 |
| 6 | 10.0 | i.p. | 1 | Day −5 |
| N3 7 | 0.1 | i.p. | 1 | Day −5 |
| | | per os | 4 | Daily starting day −4 |
| 8 | 1.0 | i.p. | 1 | Day −5 |
| | | per os | 4 | Daily starting day −4 |
| 9 | 10.0 | i.p. | 1 | Day 5 |
| | | per os | 4 | Daily starting day −4 |

Results:

TABLE 4

| Scheme of treatment | Mortality: Dead/Total Days of examination | | | | | | |
|---|---|---|---|---|---|---|---|
| | 3 | 4 | 5 | 6 | 7 | 10 | 11 | 14 |
| N1 1 | 9/10 | 1/1 | | | | | | |
| 2 | 7/10 | 2/3 | | | | | | |
| 3 | 1/10 | 1/8 | 1/8 | 2/7 | 1/5 | 0/4 | 0/4 | 0/4 |
| N2 4 | 6/10 | 2/4 | 2/2 | | | | | |
| 5 | 0/10 | 0/10 | 4/10 | 1/6 | 0/5 | 1/5 | 0/4 | 0/4 |
| 6 | 0/10 | 6/10 | 3/4 | 0/1 | 0/1 | 0/1 | 0/1 | 0/1 |
| N3 7 | 3/10 | 1/7 | 3/6 | 1/3 | 0/2 | 0/2 | 0/2 | 0/2 |
| 8 | 5/10 | 3/5 | 1/2 | 0/1 | 0/1 | 0/1 | 0/1 | 0/1 |
| 9 | 2/10 | 2/8 | 0/6 | 1/6 | 0/5 | 0/5 | 0/5 | 0/5 |
| Control 10 | 7/10 | 3/3 | | | | | | | by mouth and at 1 and 10 mg/kg by i.p. injection increased mean survival time (MST) and the absolute number of survivors when given five days prior to challenge. MIMP at 0.1 to 10 mg/kg increased MST and survivors when given a combined treatment of both i.p. and p.o. from five days prior to challenge.

Example 9

Effect of a Protected-IMP On Salmonella Infection

Protocol:

Infection. A mouse adapted *Salm. typhimurium* strain 415 (Gamaleya Research Institute, Academy Medical Science, Russia) in a dose of $5 \times 10^4$ cells in 0.5 ml PBS (pH=7.4) was injected per mouse i.p. The doses were determined so as to provide 100% mortality by day 6 with a mean survival time of 2.5 days.

Treatment. Solutions with various concentrations of MIMP (AGS-36-217) were administered parenterally as set forth in Table 5 and the results of the treatments are set forth in Table 6 herein below:

TABLE 5

Different treatment for anti-infection protection

| Scheme | MIMP Dose | Route | Sequence | Treatment (hours prior and after inoculation) |
|---|---|---|---|---|
| N1 1 | 0.1 | i.p. | 1 | −24 hours |
| 2 | 1.0 | i.p. | 1 | −24 hours |

TABLE 5-continued

Different treatment for anti-infection protection

| Scheme | MIMP Dose | Route | Sequence | Treatment (hours prior and after inoculation) |
|---|---|---|---|---|
| 3 | 10.0 | i.p. | 1 | −24 hours |
| N2 4 | 0.1 | i.p. | 1 | −4 hours |
| 5 | 1.0 | i.p. | 1 | −4 hours |
| 6 | 10.0 | i.p. | 1 | −4 hours |
| N3 7 | 0.1 | i.p. | 1 | +4 hours |
| 8 | 1.0 | i.p. | 1 | +4 hours |
| 9 | 10.0 | i.p. | 1 | +4 hours |
| N4 10 | 0.1 | i.p. | 1 | +24 hours |
| 11 | 1.0 | i.p. | 1 | +24 hours |
| 12 | 10.0 | i.p. | 1 | +24 hours |

TABLE 6

Protective effect of MIMP in experimental infection (S. tymphimurium)

| Scheme of treatment | Mortality: Dead/Total Days of examination | | | | | | | |
|---|---|---|---|---|---|---|---|---|
| | 0 | 2 | 3 | 4 | 5 | 6 | 8 | 14 |
| N1 0.1 | 0/20 | 0/20 | 4/20 | 6/16 | 4/10 | 4/6 | 2/2 | — |
| 1.0 | 0/20 | 0/20 | 0/20 | 6/20 | 12/14 | 0/2 | 2/2 | — |
| 10.0 | 0/20 | 2/20 | 4/18 | 6/14 | 2/8 | 2/6 | 2/4 | 0/2 |
| N2 0.1 | 0/20 | 2/20 | 2/18 | 8/18 | 4/10 | 4/6 | 2/2 | — |
| 1.0 | 0/20 | 2/20 | 4/18 | 4/10 | 2/6 | 0/4 | 0/4 | 0/4 |
| 10.0 | 0/20 | 0/20 | 4/20 | 14/16 | 0/2 | 2/2 | — | — |
| N3 0.1 | 0/20 | 0/20 | 2/20 | 6/18 | 8/12 | 2/4 | 0/2 | 0/2 |
| 1.0 | 0/20 | 0/20 | 0/20 | 10/20 | 0/10 | 2/10 | 6/8 | 0/2 |
| 10.0 | 0/20 | 0/20 | 6/20 | 8/14 | 0/6 | 2/6 | 2/4 | 0/2 |
| N4 0.1 | 0/20 | 4/20 | 2/16 | 2/14 | 12/12 | — | — | — |
| 1.0 | 0/20 | 0/20 | 6/20 | 6/14 | 0/6 | 2/6 | 4/4 | — |
| 10.0 | 0/20 | 0/20 | 2/20 | 12/18 | 2/6 | 4/4 | — | — |
| Control | 0/20 | 2/20 | 14/18 | 2/4 | 2/2 | — | — | — |

Infectious dose of S. typhimurium - $5 \times 10^4$ cells per mouse.

As is shown in Table 6, the control animals all died by five days with a mean survival time of about 2.5 days. The various treatments of MIMP increased MST to about four days (p<0.01) with some long term survivors, most apparent with the treatment in N3.

Example 10

Effect of MIMP On Influenza Virus-Induced Mortality

In this model, NMRI mice were challenged with influenza virus by the aerosol method. The dose of the influenza virus was determined in control animals so that there was 80–100% mortality with a mean survival time of 8 to 11 days. Treatments with control (PBS), MIMP (100 or 200 μg/mouse) and Squalane (1%) plus MIMP (200 μg/mouse) were initiated at one day prior to infection, one hour prior to infection and one hour post infection.

Figures 16, 17:
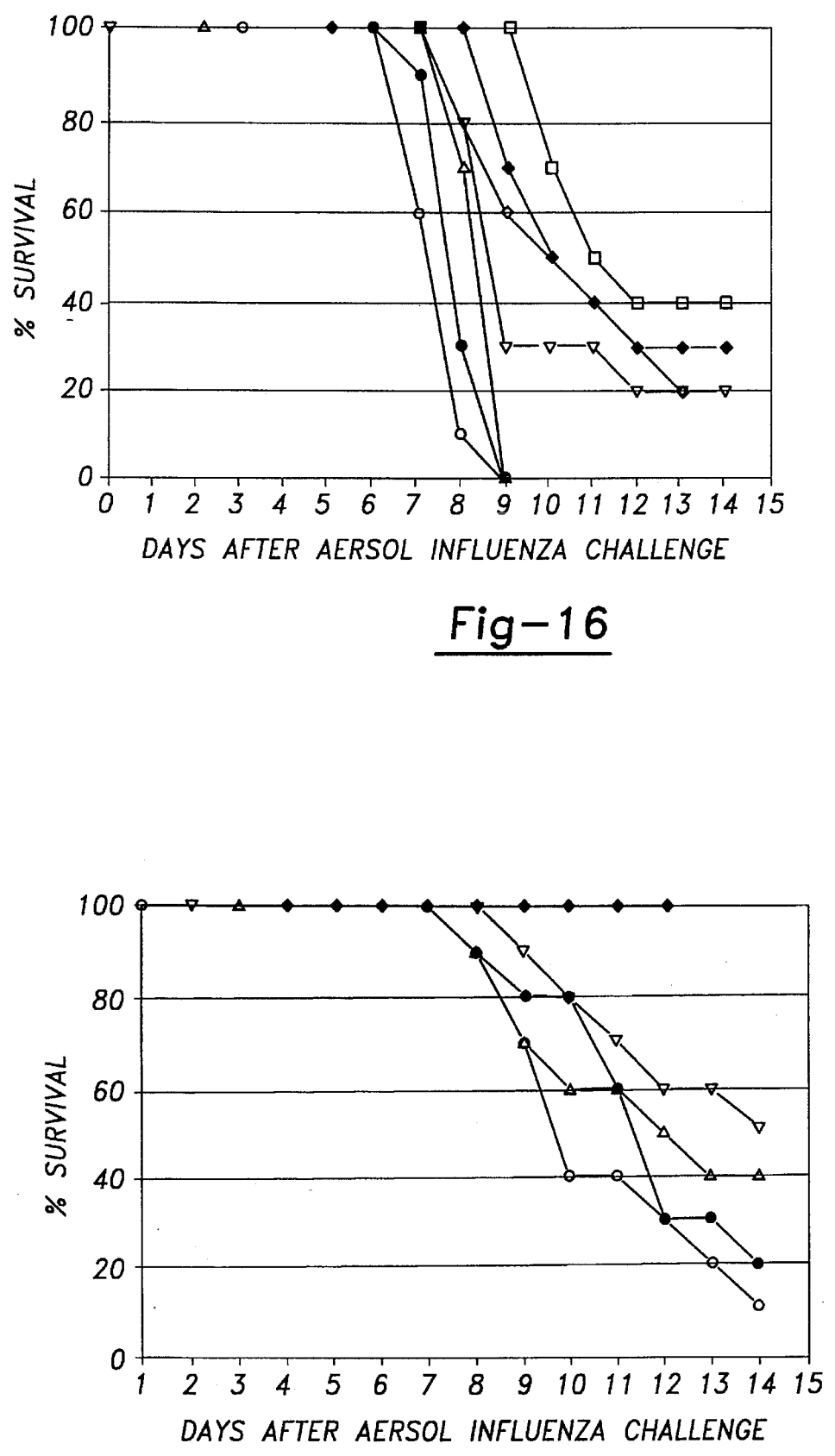

The results are set forth in Tables 7 and 8 herein below. MIMP increased the number of survivors and mean survival time (MST) when given intranasally at 200 μg/mouse (5 mg/kg) 24 hours prior (day 1) or one hour before or after challenge (Table 7). MIMP increased survival and MST when given at 100 μg/mouse only when given one hour prior to infection (FIG. 16).

In a second experiment, MIMP increased survivors and MST when given intranasally with Squalane (1%) at a dose of 200 μg/mouse one day prior to infection or one hour after infection. As shown in FIG. 17, 100% of the mice in these treatment groups survived. Squalane alone had no effect.

TABLE 7

Effect of MIMP on influenza virus-induced mortality

| Treatment | Day | Dose μg | Route | % mortality | MTD ± SD |
|---|---|---|---|---|---|
| MIMP | −1 d | 100 | i.n. | 100 | 8,7 ± 0,48 |
| | −1 h | 100 | i.n. | 100 | 7,7 ± 0,67 |
| | +1 h | 100 | i.n. | 70 | 10,0 ± 1,15 |
| | −1 d | 200 | i.n. | 60 | 10,7 ± 0,82 |
| | −1 h | 200 | i.n. | 80 | 10,0 ± 1,85 |
| | +1 h | 200 | i.n. | 80 | 9,1 ± 1,25 |
| PBS control | −1 d | | i.n. | 100 | 8,2 ± 0,63 |
| MIMP | −1 d | 100 | i.v. | 100 | 10,6 ± 1,43 |
| | −1 d | 200 | i.v. | 90 | 9,8 ± 1,64 |
| PBS control | −1 d | | i.v. | 100 | 8,2 ± 1,3 |
| untreated control | | | | 100 | 8,5 ± 0,97 |

TABLE 8

Effect of MIMP on influenza virus-induced mortality

| Treatment | Day | Dose μg | Route | % mortality | MTD ± SD |
|---|---|---|---|---|---|
| MIMP | −1 d | 200 | i.v. | 90 | 10,6 ± 1,13 |
| | +1 h | 200 | i.v. | 70 | 9,9 ± 1,57 |
| MIMP + 1% Squalane | −1 d | 200 | i.v. | 70 | 11,0 ± 1,82 |
| MIMP + 1% Squalane | +1 h | 200 | i.v. | 80 | 9,8 ± 1,67 |
| PBS control | −1 d | | i.v. | 90 | 9,8 ± 1,01 |
| MIMP | −1 d | 200 | i.n. | 50 | 11,2 ± 1,92 |
| | +1 h | 200 | i.n. | 60 | 10,2 ± 1,94 |
| MIMP + 1% Squalane | −1 d | 200 | i.n. | 0 | — |
| MIMP + 1% Squalane | +1 h | 200 | i.n. | 0 | — |
| PBS control | −1 d | | i.n. | 80 | 11,1 ± 1,89 |

Example 11

Stimulation of Antibody Response to HBsAg

Previous studies were used to select the DBA/2 murine strain as poor responders in antibody production to HBsAg (Walker et al., 1981).
Normal (control) DBA/2 mice
The results of anti-HBs detection in the control group of mice treated with HBsAg alone and in the groups treated with the combination of HBsAg and MIMP, as prepared in the examples, are presented in Table 9. The various vaccination schedules are provided in the following list.

| Scheme | Treatment |
|---|---|
| 1 | HBsAg only |
| 2 | HBsAg + MIMP per os (30 minutes prior to vaccine |
| 3 | HBsAg + MIMP i.p. simultaneously then every 4 days MIMP per os |
| 4 | HBsAg + MIMP i.p. simultaneously |
| 5 | Radiation + HBsAg |
| 6 | Radiation + scheme N2 |
| 7 | Radiation + scheme N3 |
| 8 | Control |

TABLE 9

Effect of MIMP on anti-HBs production in DBA/2 mice

| Scheme No. | Days After Injection | |
|---|---|---|
| | Day 14 | Day 21 |
| HBsAg #1 | <10 IU/l | 260 IU/l ± 16.3 |
| Scheme #2 | <10 IU/l | *370 IU/l ± 18.5 |
| Scheme #3 | **100 IU/l ± 12,6 | **610 IU/l ± 24.3 |
| Scheme #4 | **100 IU/l ± 12,6 | *420 IU/l ± 20.6 |
| Control #8 | <10 IU/l | |

*$0.01 < p < 0.05$
**$p < 0.01$

Antibody responses obtained with combined administration of HBsAg and MIMP according to the various schemes exceeded the antibody level in the control group of animals. Immunocompromised DBA/2 mice In a second set of experiments, the effect of MIMP on the induction of a specific immune response to HBsAg in immunocompromised DBA/2 mice subjected to ionizing radiation was analyzed using the same vaccination schemes as set forth for the control DBA/2.

The results of anti-HBs detection in the irradiated mice of the control group (injected only with HBsAg) and those treated with the combination (HBsAg and MIMP using schemes 2 and 3) are presented in Table 10.

TABLE 10

Effect of MIMP on anti-HBs responses in immunocompromised irradiated DBA/2 mice

| Scheme No. | Days After Injection | |
|---|---|---|
| | Day 14 | Day 21 |
| Scheme #5 | <10 IU/l | <10 IU/l |
| Scheme #6 | <10 IU/l | **100 IU/l ± 10.8 |
| Scheme #7 | <10 IU/l | **100 IU/l ± 10.0 |
| Control | <10 IU/l | <10 IU/l |

*$p < 0.01$

The data indicate that in the case of schemes 2 and 3, anti-HBs were significantly increased on day 21 indicating a restoring effect of MIMP upon the immune system of these irradiated animals.

The results presented in Example 11 demonstrate that a protected-IMP derivative is able to influence the development of humoral immune response to HBsAg. It was shown that MIMP as a single intraperitoneal, as well as a single oral administration dose of 50 mg/kg, can induce significant increase in the level of antibodies to HBsAg. After intraperitoneal administration with antigen, additional oral administration of MIMP did not increase its activity.

A hypothesis for the mechanism of adjuvant effect of 5'-nucleotidase resistant inosine-5'-monophosphate derivatives can be made, but it is not to be construed as limiting the present invention to this one mode of action. Nonresponsiveness to hepatitis B vaccine has been observed in hemodialysis patients (Walz et al., 1989) and in immunocompromised individuals (Hess et al., 1989). In some instances, larger vaccine doses or an increased number of doses have resulted in seroconversion (Walker et al., 1981). Soluble interleukin-2-receptor levels have been observed in these patients and the resulting impairment of interleukin-2 action through binding of available IL-2 may have an effect on response to hepatitis B vaccine (Walz et al., 1989; Meuer et al., 1989; Meuer et al., 1989) injected 40 mg doses of the vaccine followed by $1.2 \times 10^5$ units of natural interleukin-2 to 10 hemodialysis patients who were nonresponders. Four weeks later, six of the ten patients showed seroconversion although antibody levels were still below normal. MHC-linked unresponsiveness to protein or peptide antigens can also be overcome by administration of IL-2. The results of these examples suggestion that protected-IMP derivatives, as adjuvants, may be realized via T-cells and may involve interleukin-2.

Various publications throughout this application are referenced by citation or number. Full citations not provided herein above for the referenced publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Alper et al., "Genetic Prediction of Nonresponse to Hepatitis B Vaccine." *New Engl. J. Med.* 321:708 (1989).

Ames et al., "The Role of Polyamines in the Neutralization of Bacteriophage Deoxyribonucleic Acid." *J. Biol. Chem.* 235, pp. 729–775 (1960).

Benaceraf and McDevitt, "Histocompatibility-Linked Immune Response Genes." *Science* 175:273 (1972).

Bogdan et al., "Macrophage Deactivation by Interleukin 10", *J. Exp. Med.* 174:1549–1555 (1991)

Byars and Allison, "Immunologic Adjuvants: General Properties, Advantages and Limitations", in *Laboratory Methods in Immunology*, 2:40–52 (1989)

Carelli et al., "Persistent Enhancement of Cell-Mediated and Antibody Immune Responses After Administration of Muramyl Dipeptide Derivatives with Antigen in Metabolizable Oil." *Infection And Immunity* pp. 312–214, (1981).

Carswell et al., "An endotoxin-induced serum factor that causes necrosis of tumors", *Proc. Natl. Acad. Sci.* 72:3666–3670 (1975).

Celis et al., "Modulation of The Immune Response to Hepatitis B Virus By Antibodies." *Hepatology (Baltimore)* 7:563 (1987).

Chakkalath et al., "Leishmania Major-Parasitized Macrophages Augment Th2-Type T Cell Activation." *J. Immunology* 153:4378–4387 (1994).

Chambers et al., "Nucleoside Polyphosphates. VII. The Use of Phosphoramidic Acids in the Synthesis of Nucleoside-5 Pyrophosphates." *J.A.C.S.* 80:3749–3752 (1958).

Clerici and Shearer, "The TH1–TH2 hypothesis of HIV infection: new insights", *Immunology Today*, 15:575–581 (1994)

Davies and Shires, "Host defense in trauma and surgery", in *Advances in Host Defense Mechanisms*, Vol 6, Raven Press (1986)

Deinhardt, "Aspects of Vaccination Against Hepatitis B, Passive-Active Immunization Schedules And Vaccination Responses in Different Age Groups." *Scand. J. Infect. Dis.* 38 (suppl.):17 (1983).

Drews, "Novel Immunological Pathways to the Treatment of Infections." *Infection* 22, No. 3, (1994 *Fed. Proc.* 29:684 (1970).

Ferguson, "Hepatitis Vaccines." *Current Opinion in Infect. Dis.* 3:367 (1990).

Fiorentino et al., "Two types of Mouse T Helper Cell. IV. Th2 Clones Secrete a Factor that Inhibits Cytokine Production by Th1 Clones", *J. Exp. Med.*, 170:2081–2095 (December 1989)

Florentin et al., "Kinetic Studies of the Immunopharmacologic Effects of NPT 15292 in Mice." *Int. J. Immunopharmacol.* 4:225–234 (1982).

Glasky et al., "Isoprinosine, A Purine Derivative; Metabolic, Immunological And Antiviral Effects." In *Proceedings of a Symposium and Workshop on Combined Immunodeficiency Disease and Adenosine Deaminase Deficiency: A Molecular Defect*, Academic Press, Inc. New York, N.Y. (1975).

Good et al., "In vitro immunodulation and in vivo immunotherapy of retrovirus-induced immunosuppression", *Int. J. Immunopharmacol.* 13:1–8 (1991)

Grossman and Cohen, "Immunization" in *Basic and Clinical Immunology*. (Seventh Edition) Appleton & Lange, Norwalk, Conn. pp. 725–726, (1991).

Haak-Frendscho et al., "Administration of Anti-IL-4 Monoclonal Antibody 11B11 Increases the Resistance of Mice to Listeria Monocytogenes Infection." *J. Immunology* 148:3978–2985, (1992).

Hadden, "The action of immunopotentiators in vitro on lymphocyte and macrophage activation", in *The Pharmacology of Immunoregulation*, 370–383 (1978).

Hadden, "Thymomimetic Drugs." in *Immunopharmacology*, Raven Press, New York, pp. 183 (1985).

Hadden, "Immunotherapy in the Treatment of Infectious Diseases." In: *Proceedings of the Int'l. Symposium on Immunological Adjuvants*, Alan R. Liss, New York, pp. 337–349 (1987).

Hadden et al., "Effects of Levamisole and Imidazole on Lymphocyte Proliferation and Cyclic Nucleotide Levels," *Cell, Immun.*, pp. 98–103 (1975).

Hadden et al., "Lavamisole and Inosiplex: Antiviral Agents With Immunopotentiating Action." *New York Acad. Sci.* 284:139–152 (1976).

Hadden et al., "Purine Analogs as Immunodolulators" in *Progress in Immunology IV*. (Academic Press, New York) pp. 1393–1408 (1983).

Hadden et al., "Effects of T-Cell Growth Factor (Interleukin-II) and Thymic Hormones on Prothymocytes and Immature Thymocytes, Lymph." *Rep.*, pp. 49–54 (1986).

Hadden et al., "Methyl Inosine Monophosphate (MIMP)—A New Purine Immunomodulator." *Int. J. Immunopharmacol.* (abstract) 13:761 (1991b)

Hadden et al., "Methyl Inosine Monophosphate (MIMP) Restores Depressed Lymphoproliferative Response of Normal Human and Murine T Lymphocytes." *Int. J. Immunopharmacol.* (abstract) 13:762 (1991a).

Hadden et al., "Methyl Inosine Monophosphate (MIMP), A New Purine Immunomodulator For HIV Infection." *Int. J. Immunopharmacol.* 14:555 (1992).

Haraguchi et al., "Differential modulation of Th1- and Th2-related cytokine mRNA expression by a synthetic peptide homologous to a conserved domain within retroviral envelope protein", *Proc. Nat'l Acad. Sci.* (1995)

Haralambidis et al., "The synthesis of polyamide—oligonucleotide conjugate molecules", *Nucleic Acids Research* 18 (3):493–499 (1990).

Hess et al., "Active Immunization of Homosexual Men Using a Recombinant Hepatitis B Vaccine." *J. Med. Virol.* 29:229 (1989).

James et al., "Gastrointestinal, Hepatobiliary, Oral, & Dental Disease" in *Basic and Clinical Immunology*, 7th Edition) Appleton a Lange, Norwalk, Conn., pp 513–515 (1991).

Jerne et al., "The Agar Plaque Technique For Recognizing Anbtibody-Producing Cells in *Cell-Bound Antibodies*, Wistar Institute Press, Philadelphia, Pa., pp. 109–125 (1963).

Khorana, "Studies on Polynucleotides. VII. Approaches to the Marking of End Groups in Polynucleotide Chains: The Methylation of Phosphomonester Groups." *J. Am. Chem. Soc.* 81:4657–60 (1959).

MacDonald et al., "Requirement For a Bacterial Flora Beore Mice Generate Cells Capable of Mediating the Delayed Hypersensitivity Reaction to Sheep Red Blood Cells." *J. Immunol.* 122:2624–2629 (1979).

Meuer et al., "Low Dose Interleukin-2 Induces Immune Response Against HBsAg in Immunodeficient Nonresponders to Hepatitis B Vaccination." *Lancet.* 1:15 (1989).

Miller et al., "Models For the Interaction of $Zn^{2+}$ with DNA. The Synthesis and X-Ray Structural Characterization of Two Octahedral Zn Complexes With Monomethyl Phosphate Esters of 6-Oxopurine 5'-Monophosphate Nucleotides." *J. Am. Chem. Soc.* 107:1048–55 (1985).

Mills, "Viral Infections" in *Basic and Clinical Immunology*, Seventh Edition, Appleton & Lange, Norwalk, Conn., pp 651–653 (1991).

Moffat et al., "Nucleoside Polyphosphates. X. The Synthesis And Some Reactions of Nucleoside-5-Phosphoromorpholidates and Related Compounds. Improved Methods For the Preparation of Nucleoside-5-Polyphosphates." *J.A.C.S.* 83:649–58 (1961).

Mosmann and Coffman, "Th1 and Th2 Cells: Differential Patterns of Lymphokine Secretion Lead to Different Functional Properties. *Ann. Rev. Immunol.* 7:151–173 (1989)

Recommendations of the Immunization Practices Advisory Committee (ACIP). "Protection Against Viral Hepatitis" *MMWR* 39 (1990).

Reugg and Strand, "Inhibition of protein kinase C and anti-CD3-induced $Ca^{2+}$ influx in Jurkat T cells by a synthetic peptide with sequence identity to HIV-1 $gp41^{1}$", *J. Immunol.* 144:3928–3935 (1990)

Rouse and Horohov, "Immunosuppression in viral infections", *Rev. Infect. Dis.*, 8:850–872 (1986)

Sad and Mosmann "Single IL-2-Secreting Precursor CD4 T Cell can Develop into Either Th1 or Th2 Cytokine Secretion Phenotype", *J. Immunology*, 3514–3522 (1994)

Saha et al., "Immunopotentiating Activity Of A Nucleotide Derivative, Heptaminol AMP Amidate (HAA) In Mice And Spontaneously Hypertensive Rats (SHR)" *Research Communications in Chemical Pathology and Pharmacology* 57(1):117–127 (July 1987)

Saha et al., Effect of Heptaminol AMP Amidate, a New Nucleotide Derivative, on In Vitro Humoral Immunity" *Japan J. Pharmacol.* 47:63–69 (1988).

Sandrin et al., "Synthese d'esters Adenosine-5-Phosphoriques d'amino-alcohols, Comme Inhibiteurs Potentiels de l' Activation des Acides Amines." *Helvetica Chimica Acta.* 49:76–82 (1966).

Scott et al. "Role of cytokines and $CD^{+}$ T cell subsets in the regulation of parasite immunity and disease", *Immunol. Rev.* 112:161–195 (1989)

Scott, "IFN-y Modulates the Early Development of Th1 and Th2 Responses in a Murine Model of Cutaneous Leishmaniasis. *J. Immunol.* 147:3149 (1991).

Seaman, "Approaches to Immune Response Modulation" in *Basic and Clinical Immunology*, Seventh Edition, Appleton & Lange, Norwalk, Conn., pp 718–719 (1991).

Sieling et al., "IL-12 Regulates T Helper Type 1 Cytokine Responses in Human Infectious Disease." *Journal of Immunology* 153:3639–3647 (1994).

Sosa et al., "Methyl Inosine Monophosphate (MIMP) Promotes Immune Responses in Mice" *Int. J. Immunopharmacol.* (abstract) 13:762 (1991)

Sosa et al., "Potentiation of Immune Response in Mice By a New Inosine Derivative—Methyl Inosine Monophosphate (MIMP), *Int. J. Immunopharmacol.* 14:1259, 1266 (1992).

Stites and Terr, *Basic and Clinical Immunology* Seventh Edition, Appleton a Lange, Norwalk, Conn., pp 637–645, 646–656, 797 (1991).

Subash et al., "Single IL-2-Secreting Precursor CD4 T Cell Can Develop into Either Th1 or Th2 Cytokine Secretion Phenotype." *Journal of Immunology* 153:3514–3522 (1994).

Tepper, "Cytokines and strategies for anticancer vaccines", *Contemp. Oncol.*, 4:38–53 (1993)

Thomson et al., "The Genetic Analysis of HLA And Disease" in *HLA and Disease*, Munksgaard, Copenhagen. pp. 84–93 (1977).

Touraine et al., "In vitro Effects of Inosine 5'-Methyl Monophosphate (MeIMP) On Human Prothymocyte Differentiation", *Int. J. Immunopharmacol.* 13:761 (1991).

Trinchieri, "Interleukin-12 and Its Role in the Generation of Th1 Cells", *Immunol. Today.* 14:335 (1993).

Tripp et al., "Neutralization of IL-12 Decreases Resistance to Listeria in SCID and C.B-17 Mice." *J. Immunology* 152:1883–1887 (1994).

Turner et al., "Studies on Polynucleotides. VI Experiments On The Chemical Polymerization of Mononucleotides. Oligonucleotides Derived From Thymidine-3'-Phosphate." *J. Am. Chem. Soc.* 81:4651–56 (1959).

Walker et al., "Genetics of anti-HBs Responsiveness. I. HLA-DR7 and Nonresponsiveness to Hepatitis Vaccination" *Transfusion* (Philadelphia) 21a:601 (1981).

Walz et alo, "Factors Influencing the Response to Hepatitis B Vaccination of Hemodialysis Patients" *Nephron* 51:474 (1989).

Wilson and Fudenberg, "Controversy About Transfer Factor Therapy Nearing An End?" *Immunology Today,* 4:157 (1983)

Wybran et al., "Inosiplex (Isoprinosine): a Review of its Immunological and Clinical Effects in Disease", in *Advances in Pharmacology and Therapeutics II,* 6:123–131 (1982).

We claim:

1. A method of potentiating the immune response of a mammal in need of treatment of immunogenic stimuli comprising administering to the mammal an immunopotentiating effective amount of a 5'-nucleotidase resistant compound of the formula

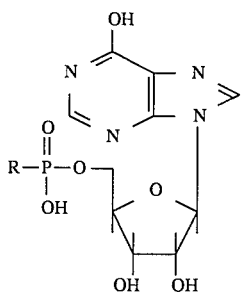

wherein R is a moiety inhibits hydrolysis of the compound by 5'-nucleotidase and is selected from the group consisting of an alkyl, alkoxy and arginine.

2. The method of potentiating the immune response as set forth in claim 1 wherein the mammal in need of treatment of immunogenic stimuli is HIV-infected.

3. The method of potentiating the immune response as set forth in claim 1 wherein the mammal in need of treatment of immunogenic stimuli has cancerous tumors.

4. The method of potentiating the immune response as set forth in claim 1 wherein the effective amount of a 5'-nucleotidase resistant inosine-5'-monophosphate compound is from 1–50 mg/kg body weight at least daily.

5. A method for treating viral and intracellular bacterial pathogens in a mammal including the steps of diagnosing a patient having an infectious disease caused by a pathogen selected from the group consisting of intracellular bacterial and viral pathogens;

and administering an effective amount of an immune stimulator 5'-nucleotidase resistant inosine-5'-monophosphate having the formula

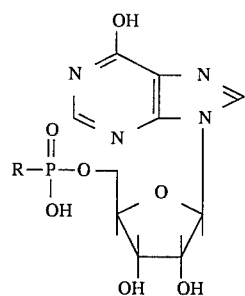

wherein R is selected from the group consisting of
a) an alkyl group from 1–6 carbon atoms, and
b) an alkoxy group having the formula —OR$^1$, wherein R$^1$ is an alkyl group of from about 1–6 carbon atoms.

6. The method of claim 5, wherein R is the group —OR$^1$ and R$^1$ is methyl.

7. The method of claim 5, wherein R is methyl.

8. The method of claim 5 wherein the amount administered is 1–50 mg/kg body weight at least daily.

9. A method for treating viral and intracellular bacterial pathogens in a mammal including the steps of diagnosing a patient having an infectious disease caused by a pathogen selected from the group consisting of intracellular bacterial and viral pathogens;

and administering an effective amount of an immune stimulator 5'-nucleotidase resistant inosine-5'-monophosphate having the formula

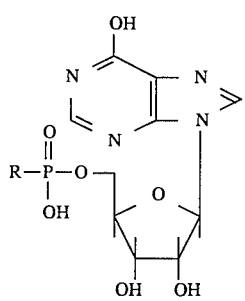

wherein R is selected from the group consisting of
a) an alkyl group from 1–6 carbon atoms, and
b) an alkoxy group having the formula —OR$^1$, wherein R$^1$ is an alkyl group of from about 1–6 carbon atoms; and administering an effective amount of Squalane.

10. The method of claim 9, wherein R is the group —OR$^1$ and R$^1$ is methyl.

11. The method of claim 9, wherein R is methyl.

12. The method of claim 9 wherein the infectious disease being treated is influenza.

13. The method of claim 9 wherein the amount administered of the 5'-nucleotidase resistant inosine-5'-monophosphate is 1–50 mg/kg body weight at least daily, and the amount of Squalane administered is 1–5 ml at least daily.

14. A method of determining patients who will benefit from treatment with 5'-nucleotidase resistant inosine-5'-monophosphates including the steps of isolating peripheral blood lymphocytes;

performing a lymphocyte stimulation assay in vitro in the presence of a mitogen and a 5'-nucleotidase resistant inosine-5'-monophosphate;

identifying patients with a depressed in vitro response to the 5'-nucleotidase resistant inosine-5'-monophosphate whereby such patients are not candidates for treatment with the 5'-nucleotidase resistant inosine-5'-monophosphate.

15. The method of claim 16 wherein the mitogen is phytohemagglutinin.

16. The method of claim 16 wherein the 5'-nucleotidase resistant inosine-5'-monophosphate is selected from the group consisting of Methyl-5'-inosine-monophosphate (Methyl-IMP or Me-IMP), methyl-5'-inosine-phosphonate (Mp-IMP), ethyl-5'-inosine-monophosphate (Ethyl-IMP or E-IMP), arginine-5'-inosine-monophosphate (Arginine-IMP or Arg-IMP) and (Heptamin-1-ol)-5'-inosine-monophosphate (Ha-IMP).

17. A method of treating tumor bearing patients including the steps of identifying patients with tumors;

administering an effective amount of an immune stimulator 5'-nucleotidase resistant inosine-5'-monophosphate having the formula

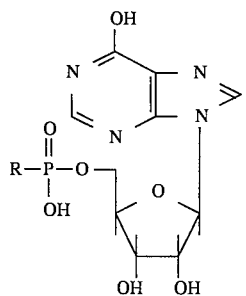

wherein R is selected from the group consisting of
a) an alkyl group from 1–6 carbon atoms, and
b) an alkoxy group having the formula —OR$^1$, wherein R$^1$ is an alkyl group of from about 1–6 carbon atoms; and administering an effective amount of endotoxin.

18. The method of claim 17 wherein the endotoxin is selected from the group consisting of lipopolysaccharide and salmonella vaccine.

19. A method of making inosine-5'-monophosphate resistant to 5'-nucleotidase by chemically modifying a inosine-5'-monophosphate to the formula:

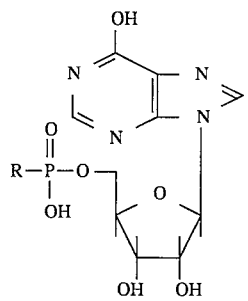

wherein R is selected from the group consisting of an alkyl, alkoxy and secondary amino compounds whereby inosine-5'-monophosphate biological activity is retained in vitro and extended to in vivo.

20. The method of claim 19 wherein the step of chemically modifying includes condensing with one of alcohol, ether and a secondary amino compound.

21. The method of claim 20 wherein dicyclohexylcarbodiimide is used as a condensing agent.

22. The method of claim 20 wherein the alcohol is selected from the group consisting of methyl alcohol, ethyl alcohol, n-propyl alcohol, n-butyl alcohol, n-pentyl alcohol and n-hexyl alcohol.

23. The method of claim 20 wherein the ether is selected from the group consisting of methyl ether, ethyl ether, propyl ether, butyl ether, pentyl ether and hexyl ether.

24. The method of claim 20 wherein the secondary amino compound is arginine.

25. The method of claim 20 wherein the secondary amino compound is a peptide linked through its N-terminal to the phosphorus atom.

26. The method of claim 25 wherein the peptide is selected from the group consisting of ARG-PRO, ARG-PRO-LYS and ARG-PRO-LYS-THR.

27. A method of preparing inosine-5'-monophosphate resistant to 5'-nucleotidase including the steps of blocking the nucleotide of 2',3'-isopropylideneinosine, reacting the blocked 2',3'-isopropylideneinosine with methylphosphonic dicloride; and deblocking the nucleotide to yield methyl-5'-inosine monophosphonate.

* * * * *

UNITED STATES PATENT AND TRADEMARK OFFICE
CERTIFICATE OF CORRECTION

PATENT NO. : 5,614,504

DATED : March 25, 1997

INVENTOR(S) : John W. Hadden; Alfredo Giner-Sorolla

It is certified that error appears in the above-identified patent and that said Letters Patent is hereby corrected as shown below:

Column 40 line 8 through Column 42 line 51 should be deleted from the Patent.

Signed and Sealed this

Thirty-first Day of March, 1998

*Attest:*

*Attesting Officer*

BRUCE LEHMAN

*Commissioner of Patents and Trademarks*